United States Patent [19]
Robinson

[11] Patent Number: 5,225,196
[45] Date of Patent: * Jul. 6, 1993

[54] BIOADHESIVE COMPOSITIONS AND METHODS OF TREATMENT THEREWITH

[75] Inventor: Joseph R. Robinson, Madison, Wis.

[73] Assignee: Columbia Laboratories, Inc., Hollywood, Fla.

[ * ] Notice: The portion of the term of this patent subsequent to Jan. 8, 2008 has been disclaimed.

[21] Appl. No.: 638,184

[22] Filed: Jan. 7, 1991

Related U.S. Application Data

[63] Continuation of Ser. No. 287,464, Dec. 20, 1988, Pat. No. 4,983,392, which is a continuation of Ser. No. 909,960, Sep. 22, 1986, Pat. No. 4,795,436, which is a continuation of Ser. No. 690,483, Dec. 20, 1984, Pat. No. 4,615,697, which is a continuation of Ser. No. 551,295, Nov. 14, 1983, abandoned.

[51] Int. Cl.$^5$ ............................................. A61F 13/00
[52] U.S. Cl. ................................ 424/427; 424/449; 514/177
[58] Field of Search .................. 424/427, 428, 434; 514/177

[56] References Cited

U.S. PATENT DOCUMENTS

| | | | |
|---|---|---|---|
| 3,202,577 | 8/1965 | Markus | 167/55 |
| 3,630,200 | 12/1971 | Higuchi | 424/427 |
| 3,641,237 | 2/1972 | Gould et al. | 424/427 |
| 3,811,444 | 5/1974 | Heller et al. | 424/428 |
| 3,935,303 | 1/1976 | Khromov et al. | 424/427 |
| 3,946,106 | 3/1976 | Chuen et al. | 424/427 |
| 3,962,414 | 6/1976 | Michaels | 424/473 |
| 3,981,303 | 9/1976 | Higuchi et al. | 424/425 |
| 4,180,646 | 12/1979 | Choi | 424/426 |
| 4,186,184 | 1/1980 | Zaffaroni | 424/427 |
| 4,304,765 | 12/1981 | Shell et al. | 424/427 |
| 4,357,259 | 11/1982 | Senyei | 264/4.3 |
| 4,483,846 | 11/1984 | Koide | 424/433 |
| 4,983,392 | 1/1991 | Robinson | 424/427 |

OTHER PUBLICATIONS

Derwent Accession No. 82-80239E/38.

*Primary Examiner*—Thurman K. Page
*Assistant Examiner*—Leon R. Horne
*Attorney, Agent, or Firm*—Weil, Gotshal & Manges

[57] ABSTRACT

A controlled release treatment composition method of use are disclosed. The composition includes a bioadhesive and an effective amount of a treating agent. The bioadhesive is a water-swellable, but water-insoluble, fibrous, cross-linked carboxy-functional polymer containing (a) a plurality of repeating units of which at least about 80 percent contain at least one carboxyl functionality, and (b) about 0.05 to about 1.5 percent cross-linking agent substantially free from polyalkenyl polyether.

19 Claims, 6 Drawing Sheets

MODIFIED SURFACE TENSIOMETER

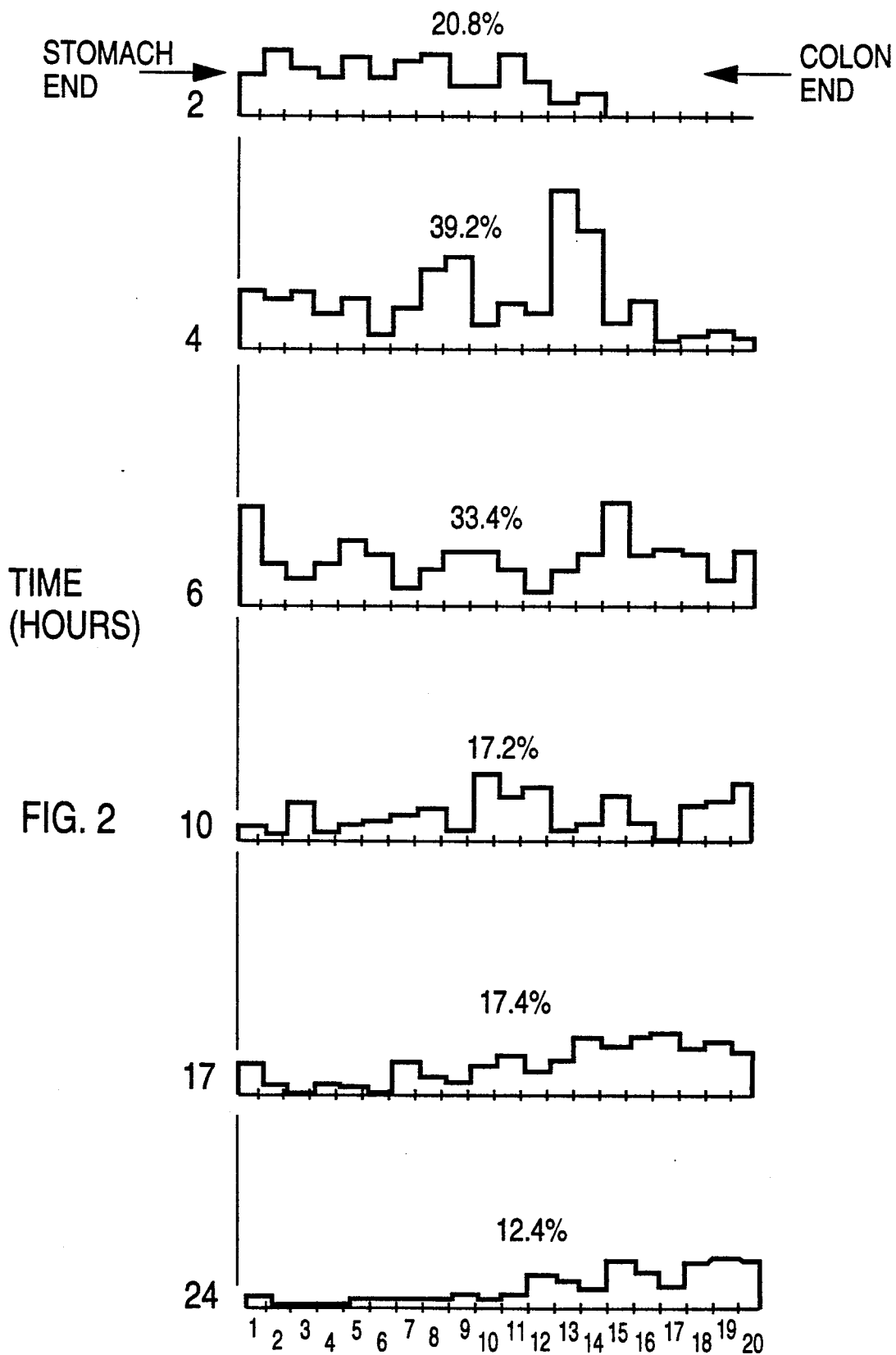

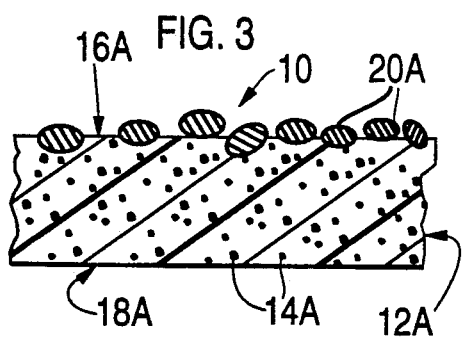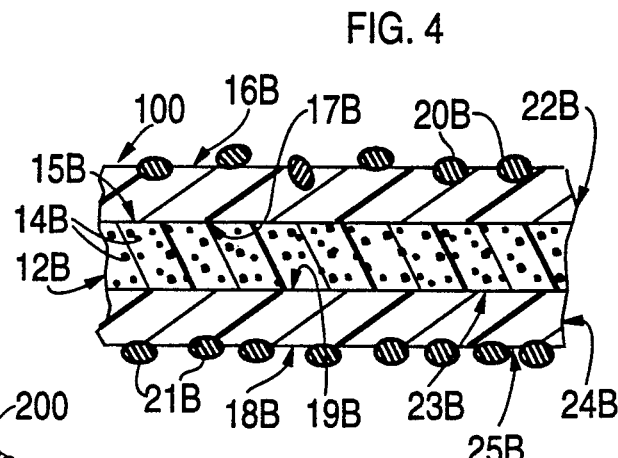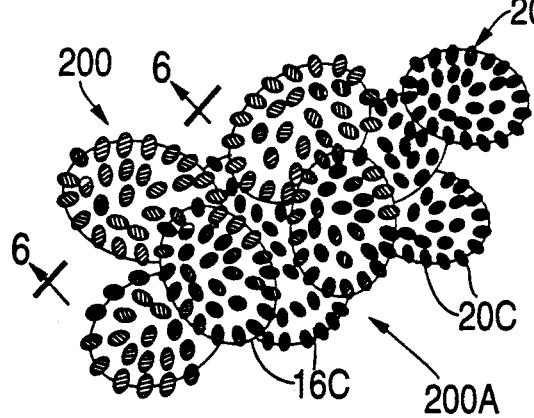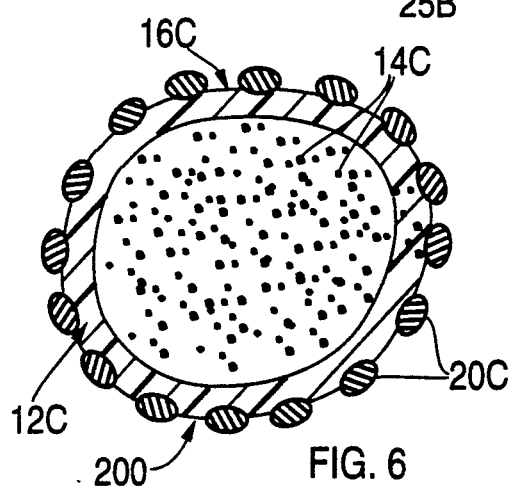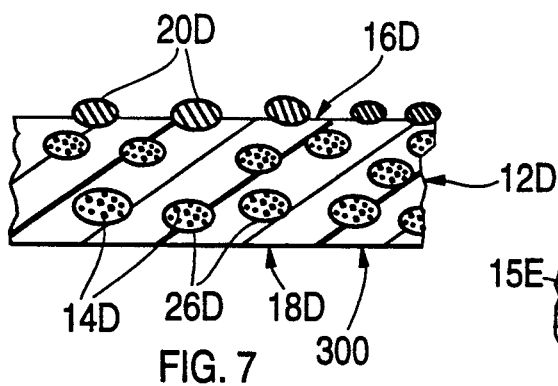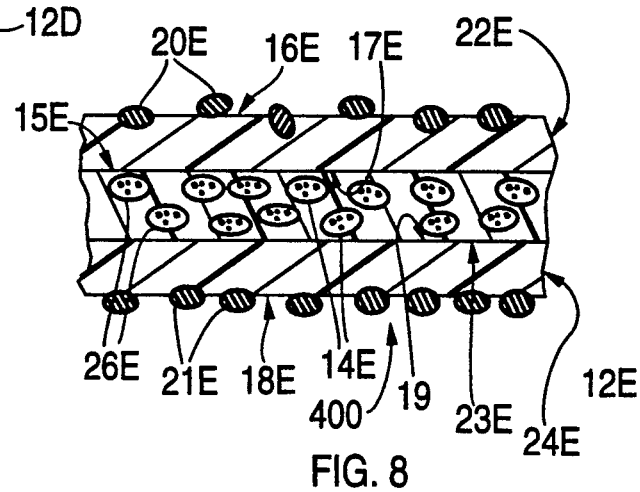

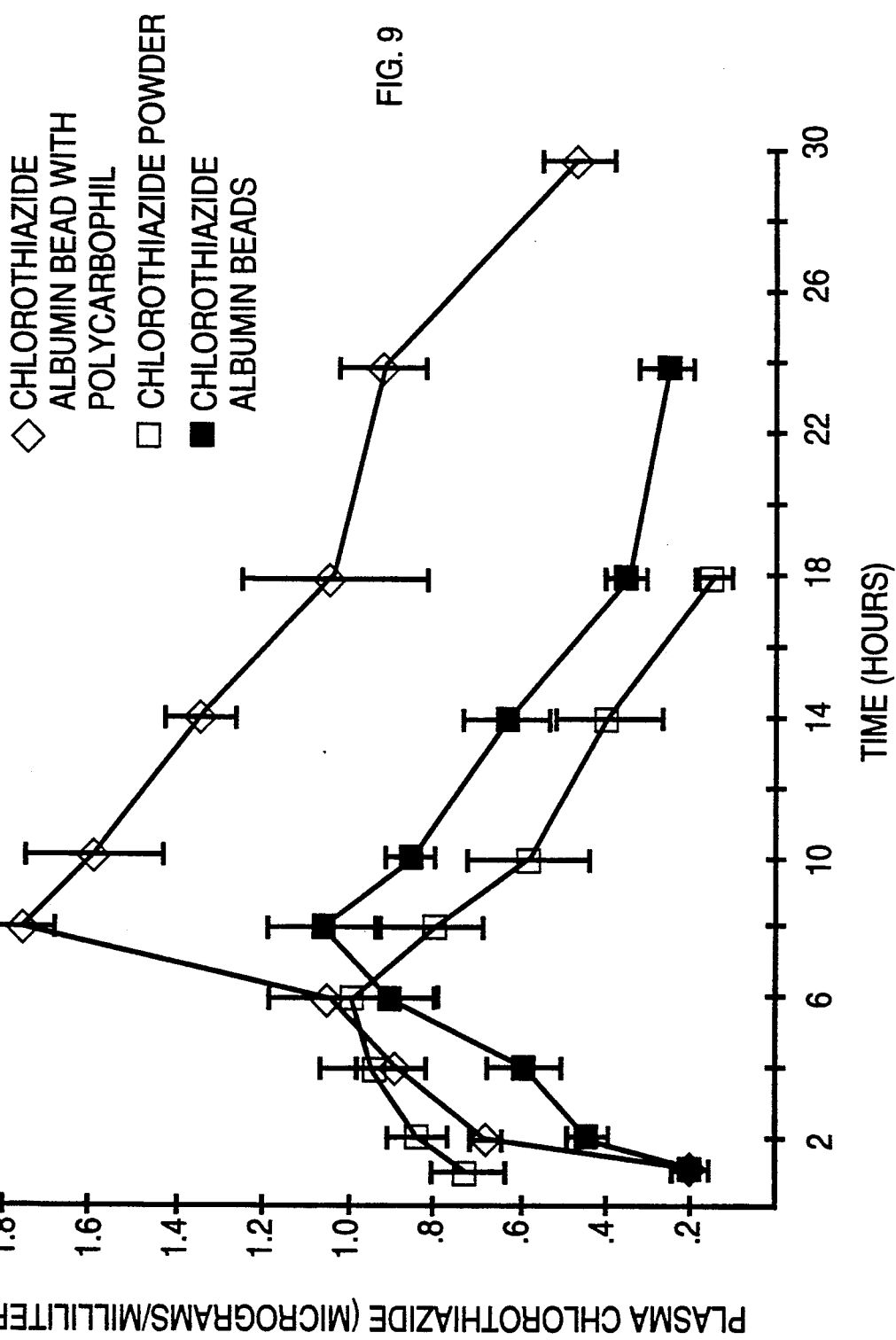

BIOADHESIVE COMPOSITIONS AND METHODS OF TREATMENT THEREWITH

CROSS-REFERENCE TO RELATED APPLICATION

This is a continuation of co-pending application Ser. No. 07/287,464, filed on Dec. 20, 1988, now U.S. Pat. No. 4,983,392, which was a continuation of co-pending application Ser. No. 909,960, filed on Sep. 22, 1986, now U.S. Pat. No. 4,795,436, which was a continuation of co-pending application Ser. No. 690,483, filed on Dec. 20, 1984, now U.S. Pat. No. 4,615,697, which was a continuation-in-part of co-pending application Ser. No. 551,295, filed Nov. 14, 1983, now abandoned.

TECHNICAL FIELD

The present invention contemplates compositions for treatment of skin and mucus membrane, and particularly contemplates controlled release compositions and methods of treatment that include bioadhesives.

BACKGROUND ART

Controlled release of an active agent; i.e., release of the active agent over a period of time, has been a source for considerable research effort over the past twenty to thirty years. Exemplary of systems that utilize controlled release of an active agent are microcapsules containing medicaments as are illustrated in U.S. Pat. No. 3,242,051 and U.S. Pat. No. 3,041,289. Substantially inert plastic matrices containing an active agent such as a pesticide dissolved or dispersed therein as are illustrated by U.S. Pat. No. 3,590,119, U.S. Pat. No. 3,639,583, and U.S. Pat. No. 4,012,221, exemplify yet another class of controlled release system.

Several materials, which in the presence of water adhere to the skin and/or mucus membranes, have been used by themselves or in conjunction with one or more active agents to treat various pathological conditions. Exemplary of such materials are the complex of sulfated sucrose and aluminum hydroxide known generically as sucralfate and available under the trademark CARAFATE® from Marion Laboratories, Inc. of Kansas City, Mo. Sucralfate is used alone or in conjunction with an antacid to treat duodenal ulcers. Another adherent material, designed for use in the buccal cavity, is a combination of gelatin, pectin and sodium carboxymethylcellulose in a plasticized hydrocarbon gel available under the trademark ORABASE® from Hoyt Laboratories Division of Colgate-Palmolive Co. of Needham, Mass. A mucosal adherent ointment based upon partly neutralized polymethacrylic acid methyl ester was recently reported by Bremecher et al., *Arzneim.-Forsch./Drug Res.*, 33, 591 (1983). That ointment was reported to show a pseudoplastic quality without any thixotropic effect, good mucosal adhesion and no local irritation.

A sustained release compressed tablet is described in U.S. Pat. No. 3,065,143. The tablet is reported to contain a medicinal agent and a hydrophilic gum that hydrates rapidly and swells in aqueous fluids at body temperature. Several naturally occuring and synthetic gums are said to be useful. Particularly useful gums disclosed include hydroxypropyl methyl cellulose ethers, sodium carboxy methyl cellulose, a material described as carboxy polymethylene, and mixtures thereof.

Delayed release pharmaceuticals are also disclosed in U.S. Pat. No. 3,074,852. The compositions of this patent are disclosed to contain a medicinal component and a polymer carrier. The polymer carrier is disclosed as being a polymer of U.S. Pat. No. 2,798,053, prepared by polymerization of 0.75 to 2 percent by weight polyalkenyl polyether as cross-linking agent with acrylic acid, or its equivalent.

The polymerization is reported to be carried out in a hydrocarbon diluent with a free radical catalyst. The polymer of particular interest in U.S. Pat. No. 3,074,852 is said to be in acid form, and is more particularly described in U.S. Pat. No. 2,909,462, which patent further describes its polymers as being agglomerated by steam action. That particularly described polymer is reported to be the material sold as CARBOPOL® 934 by B. F. Goodrich Chemical Company.

U.S. Pat. No. 3,330,729 discloses tablets that contain a basic, pharmaceutically acceptable calcium or magnesium salt such as magnesium oxide, calcium oxide or calcium hydroxide admixed with a medicament and a cross-linked acrylic acid polymer. The cross-linked polymer utilized in those tablets is said to be described in U.S. Pat. No. 2,798,053, and contains acrylic acid cross-linked with about 0.75 to about 2 percent by weight of the polymer of a copolymerized polyalkenyl polyether. Exemplary polyalkenyl polyethers are disclosed as polyallyl sucrose or polyallyl pentaerythritol that are said to desirably contain an average of at least 3 allyl groups per molecule, the allyl groups being bonded by ether linkages. The exemplary, cross-linked polymer is again said to be CARBOPOL® 934.

U.S. Pat. No. 4,327,725 discloses an osmotic device that includes a semi-permeable wall surrounding a compartment housing (a) an agent (e.g., a drug) that is insoluble to very soluble in aqueous and biological fluids, and (b) a layer of a fluid, swellable, hydrogel. A large number of hydrogels are disclosed including neutral, anionic and cationic materials. The hydrogel is said to function in this device by imbibing an aqueous fluid, swelling, and thereby exerting a force against the solution or suspension of the agent, whereby the agent is dispensed through the semi-permeable wall.

A controlled release system based on a neutral hydrogel of a polymer of ethylene glycol methacrylate or similar monomer cross-linked sufficiently to make the polymer insoluble is disclosed in U.S. Pat. No. 3,551,556 Example 8 of that patent also discloses an acid-containing hydrogel prepared by the copolymerization of methacrylic acid and maleic anhydride to form what appears to be a linear, noncross-linked polymer. Drug concentration from that hydrogel delivery system was reported to soon reach a maximum and then decrease according to a flat, logarithmic curve.

Drug-dispensing films are disclosed in U.S. Pat. No. 3,641,237. The films of that patent are disclosed to be prepared by polymerization of lower alkoxy lower alkyl acrylates and methacrylates along with a 0–40 percent of a hydrophilic acrylic monomer in the presence of a cross-linking agent. Various monomers are disclosed as useful for the 0–40 percent co-monomers, including hydroxyalkyl acrylates and methacrylates, salts of alpha,beta-unsaturated organic acids and strong acid salts of polymerizable ethylenically unsaturated amine-containing monomers.

European Patent Office Publication No. A10 043 319 discloses copolymers capable of absorbing and progressively liberating pharmaceutically active substances. The useful copolymers are disclosed to contain about 30 to 80 percent acrylate or methacrylate alkyl monoester, about 5 to 68 percent acrylic or methacrylic acid and about 2 to about 15 percent of a bi- or tri-functional acrylate or methacrylate ester. Exemplary bi-functional ester cross-linking agents are ethylene and polyethylene glycol diacrylates. Trimethylolpropane triacrylate and triethylolpropane trimethacrylate are exemplarly tri-functional esters.

U.S. Pat. No. 4,226,848 discloses a composition for adhering a pharmaceutical preparation to the mucosa of the oral or nasal cavities. The composition disclosed contains a water-swellable and mucosa-adherent polymeric matrix comprising (a) about 50 to about 95 percent by weight of a cellulose ether and (b) about 50 to about 5 percent by weight of a homo- or copolymer of acrylic acid or a pharmaceutically acceptable salt thereof, with a pharmaceutically effective amount of a medicament dispersed therein.

It is stated in that patent that when either material of the adherent composition is used singly in producing a pharmaceutical preparation, the resulting preparation is unsuitable as a slow-releasing preparation because it does not adhere to the mucosa of the oral or nasal cavity or even when it adheres, it is relatively rapidly, disintegrated, dispersed or dissolved by the saliva or other secretions. The specified ratio of the two polymers that form the polymeric matrix is reported to be essentially required in order for the slow-releasing preparation disclosed in that patent not to cause whitening of the mucosa and to release the medicament at a controlled rate. It is further reported that when the polyacrylic acid or salt portion of that composition is present at greater than about 50 percent by weight, the preparation irritates the mucosa, and causes whitening of the mucosa and the marked occurance of blisters thereon.

The polyacrylic acid or salt portion of the preparation of U.S. Pat. No. 4,226,848 is also described as being water-soluble or water-swellable, but is further described as having a desired, specific range of viscosities at a concentration of 0.2 percent by weight in water. Thus, if that polymer is not truly soluble in water, it is dispersible to at least a sufficient extent to obtain the desired viscosity. An exemplary acrylic acid polymer disclosed therein is the lightly cross-linked acrylic acid-allyl sucrose copolymer available under the trademark CARBOPOL® 934 from B. F. Goodrich Chemical Co., which is said to form a high viscosity gel-like dispersion in water.

BRIEF DESCRIPTION OF THE INVENTION

The present invention contemplates controlled release compositions and methods utilizing those compositions. The compositions include a bioadhesive and an effective amount of a treating agent. The bioadhesive comprises a water-swellable, functional polymer. That polymer contains (a) a plurality of repeating units of which at least about 80 percent contain at least one carboxyl functionality and (b) about 0.05 to about 1.5 percent cross-linking agent substantially free from polyalkenyl polyether, the percentages being based upon the weights of unpolymerized repeating units and cross-linking agent, respectively. In typical practice, the ratio by weight of the bioadhesive to the treating agent in the composition is about 200,000:1 to about 1:100.

The treating agent may be a medicinal agent such as an agent for treating a cardiovascular condition, an agent for treating an internal condition, an agent for treating a mental health condition, an antibiotic treating agent, a chemotherapeutic agent, an anti-inflammatory agent, a high molecular weight protein or polypeptide treating agent, or the like. The treating agent may also be a cosmetic agent such as a sun screen, a skin softener, an acne treating agent, or the like. The treating agent may also be a nutritional agent.

A composition of this invention may be provided in a variety of physical forms. For example, a composition may be an intimate mixture of the bioadhesive and treating agent in either dry form, as a semi-solid or as a liquid suspension. The composition may also be provided as a three-dimensional structure such as a capsule, a capsule aggregate, a film or laminate. When provided as a three-dimensional structure, the treating agent is contained in a medicinally inert matrix and the structure defines at least one surface on which the bioadhesive is disposed.

The controlled release composition adheres to the skin or to mucus membranes (mucosa) in the presence of sufficient water to swell the bioadhesive.

A controlled release method of treatment is also contemplated. According to this method, a controlled release composition of this invention is provided. An area of skin or of mucus membrane to be treated is contacted with that composition, with the contacting being carried out in the presence of sufficient water to swell the bioadhesive. The composition adheres to the area contacted, releasing the treating agent at a controlled rate, and causing the treating agent to be sorbed at least at the vicinity of the contacted area.

The contacting step may be carried out by instillation of the composition in liquid form directly onto the area to be treated such as in the precorneal pocket of the eye. Contact between the composition and treated area may also be carried out by swallowing the composition whereby the composition contacts mucosa of the gastrointestinal tract. A composition of this invention may also be inserted into the buccal, nasal, vaginal and/or anal cavities to contact the mucosa therein.

BRIEF DESCRIPTION OF THE DRAWINGS

In the figures forming a part of this disclosure,

FIG. 2 is a bar graph illustrating relative amounts of bioadhesive remaining in the small intestine of laboratory rats into whose stomachs gelatin capsules containing the bioadhesive and a radioactive label were surgically implanted;

FIG. 3 is an enlarged, diagramatic, fragmentary cross-sectional view of a composition of this invention as a film;

FIG. 4 is an enlarged, diagramatic, fragmentary cross-sectional view of a composition of this invention as a laminate;

FIG. 5 is an enlarged, diagramatic, fragmentary perspective view of an aggregate of a plurality of capsular compositions of this invention;

FIG. 6 is an enlarged, diagramatic, cross-sectional view of a composition of this invention in capsular form taken along plane 6—6 of FIG. 5;

FIG. 7 is another enlarged, diagramatic, fragmentary cross-sectional view of a composition of this invention as a film;

FIG. 8 is another enlarged, diagramatic, fragmentary cross-sectional view of a composition of this invention as a laminate;

FIG. 9 is a graph illustrating the in vivo concentration of chlorothiazide in micrograms/milliliter ($\mu$g/ml) as a treating agent over a 30 hour period in the plasma of laboratory rats as dispensed from a bioadhesive-albumin bead sustained release composition of this invention ($\Diamond$), from a control, albumin bead sustained release composition containing no bioadhesive (■), and from a control, bioadhesive-free, non-sustained release composition (□). Horizontally ended vertical lines at each datum point are error bars reported as standard error of the mean;

Figure 1:
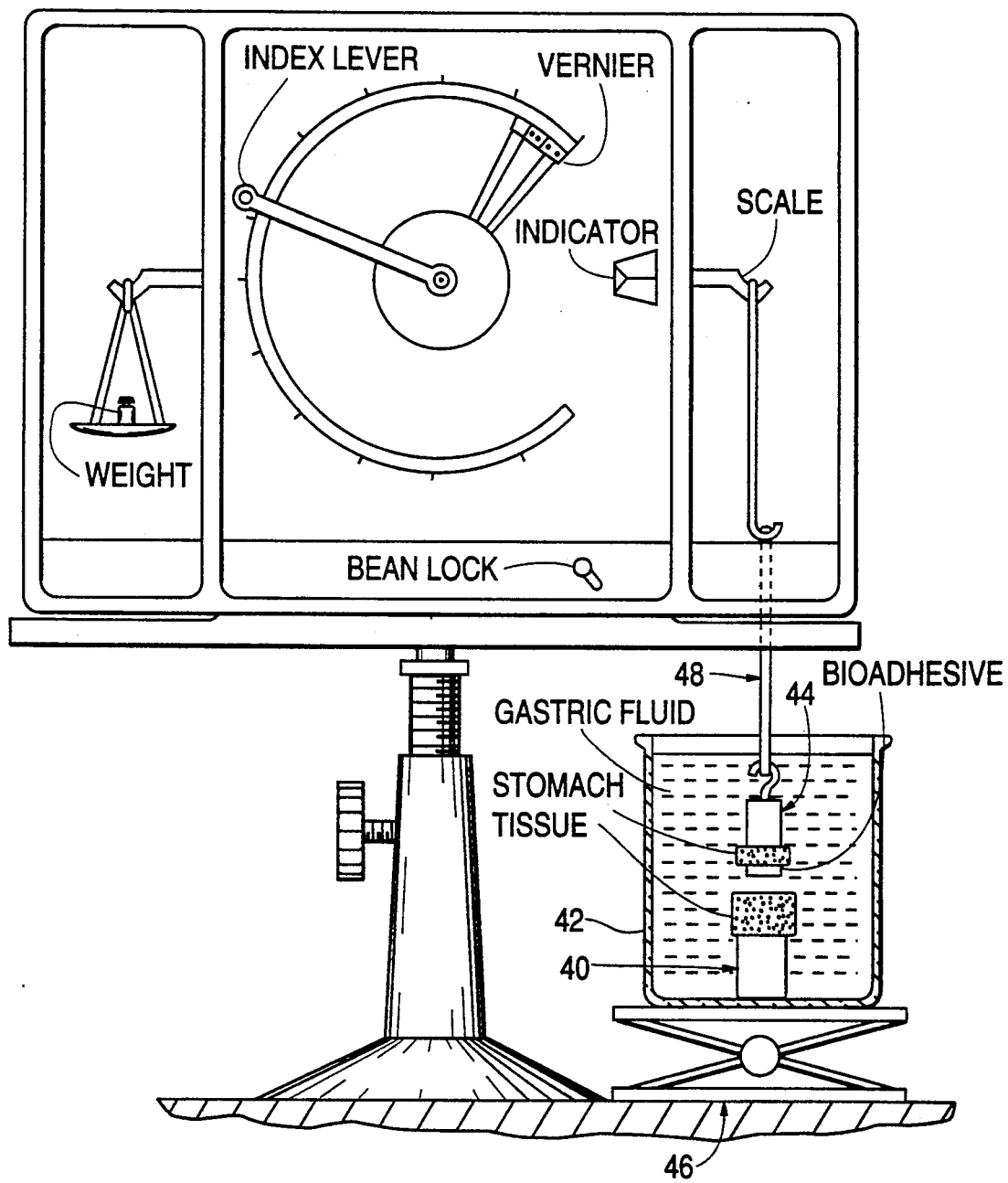
FIG. 1 illustrates a diagramatic side view of a modified, commercially available surface tensiometer utilized to measure adhesive strength of bioadhesives.

The present invention provides several advantages and benefits. Salient among those advantages is the provision of improved controlled release of a treating agent to the skin or mucosa over an extended period of time.

Another advantage of the present invention is that its compositions are not noticeably irritating to the skin or mucosa with which they are contacted.

One of the salient benefits of the present invention is that its treating agent may be substantially any medicinal agent or cosmetic agent that is a solid at ambient temperatures.

Yet another benefit of the present invention is that its compositions may be fabricated with relative ease.

Still further benefits and advantages of the present invention will be apparent to those skilled in the art from the Detailed Description, Examples and claims that follow.

DETAILED DESCRIPTION OF THE INVENTION

The present invention relates to controlled release compositions and methods of their use. The compositions themselves include an effective amount of a treating agent and a bioadhesive.

The compositions are designed for use on the skin and mucus membranes (mucosa) of an animal body, such as that of a human, to which the compositions adhere in the presence of a sufficient amount of water to swell the bioadhesive. The compositions so adhered to mucosa or skin slowly release the treating agent to the contacted body area for relatively long periods of time, and cause the treating agent to be sorbed (absorbed or adsorbed) at least at the vicinity of the contacted body area. Such time periods are longer than the time of release for a similar composition that does not include the bioadhesive as disclosed herein.

The compositions of this invention are substantially non-toxic to the animals in which or on which they are placed, aside from any toxicity associated with the treating agent alone. Thus, when contacted with and adhered to skin or mucosa, the compositions cause no apparent whitening or blistering effects due to the bioadhesive. In addition, adverse immunologic effects from the use of compositions of this invention in animals have not been noted.

The treating agents useful herein are selected generally from the classes of medicinal agents and cosmetic agents. Substantially any agent of these two classes of materials that is a solid at ambient temperatures may be used in a composition or method of the present invention. Treating agents that are liquid at ambient temperatures, e.g. nitroglycerin, can be used in a composition of this invention, but are not preferred because of the difficulties presented in their formulation.

Exemplary medicinal agents include agents for treating cardiovascular conditions such as chlorothiazide (diuretic), propranolol (antihypertensive), hydralazine (peripheral vasodilator), isosorbide or nitroglycerin (coronary vasodilators), metoprolol (beta blocker), procainamide (antiarrythmic), clofibrate (cholesterol reducer) or coumadin (anticoagulant); agents for treating internal conditions such as conjugated estrogen (hormone), tolbutamide (antidiabetic), levothyroxine (thyroid conditions), propantheline (antispasmodic), cimetidine (antacid), phenyl propanolamine (antiobesity), atropine or diphenoxalate (antidiarrheal agents), docusate (laxative), or prochlorperazine (antinauseant); agents for treating mental health conditions such as haloperidol or chlorpromazine (tranquilizers), doxepin (psychostimulant), phenytoin (anticonvulsant), levo dopa (antiparkinism), benzodiazepine (antianxiety) or phenobarbital (sedative); anti-inflammatory agents such as fluorometholone, acetaminophen, phenacetin, aspirin, hydrocortisone, or predisone; anti-histamines such as diphenhydramine hydrochloride or dexchlorpheniramine maleate; antibiotics such as sulfanilamide, sulfamethizole, tetracycline hydrochloride, penicillin and its derivatives, cephalosporin derivatives or erythromycin; chemotherapeutic agents such as sulfathiazole, doxorubicin, cisplatin or nitrofurazone; topical anaesthetics such as benzocaine; cardiac tonics such as digitalis or digoxin; antitussives and expectorants such as codeine phosphate, dextromethorphan or isoproterenol hydrochloride; oral antiseptics such as chlor hexidine hydrochloride or hexylresorcinol; enzymes such as lysozyme hydrochloride or dextronase; birth control agents such as estrogen; opthalmic treating agents such as timolol or gentamycin, and the like. In addition, medicinal treating agents may also include whole proteins such as the VP$_3$ capsid protein (also known as the VP$_{Thr}$ and VP$_1$ capsid proteins in other nomenclature systems) of foot-and-mouth disease virus described in U.S. Pat. No. 4,140,763 as being useful as the active ingredient in a vaccine against foot-and-mouth disease, insulin or interferon; polypeptide treating agents such as endorphins, human growth hormone, or bovine growth hormone, or still lower molecular weight polypeptides or conjugates of those polypeptides linked protein carriers as are described in Sutcliffe et al., *Science,* 219, 660–666 (1983). Exemplary cosmetic agents include sun screens such as p-dimethylaminobenzoic acid or glyceryl p-aminobenzoate, a skin softener such as urea, keratolytic agents such as salicylic acid; acne treating agents such as benzoyl peroxide or sulfur; perfumes, and the like. Nutritional agents such as vitamins and/or minerals like riboflavin and iron, respectively, may also comprise useful treating agents herein.

The treating agent may be used singly or as a mixture of two or more such agents.

One or more adjuvants may also be included with a treating agent, and when so used, an adjuvant is included in the meaning of the phrase "treating agent" as that phrase is used herein. Exemplary of useful adjuvants are chelating agents such as ethylenediaminetetracetic acid (EDTA) that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is present in the compositions of this invention in an amount that is sufficient to prevent, cure and/or treat a condition for a desired period of time for which the composition of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the animal in which it is used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Inasmuch as amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agents to determine the effective amount of such a treating agent for a particular composition of this invention. While the effective amount for all treating agents cannot be stated, typical compositions of this invention may contain about one microgram to about one gram of treating agent per dose administered. More preferably, a composition of this invention may contain about one microgram to about 250 milligrams per dose.

The second principle ingredient of the compositions of this invention is a bioadhesive. This bioadhesive comprises a water-swellable, but water-insoluble, fibrous, cross-linked carboxy-functional polymer. The polymer contains (a) a plurality of repeating units of which at least about 80 percent contain at least one carboxyl functionality and (b) about 0.05 to about 1.5 percent cross-linking agent substantially free from polyalkenyl polyether, with the percentages being based upon the weights of unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, the bioadhesive is a reaction product of the polymerization of only a carboxyl-functional monomer and the cross-linking agent. Also in more preferred practice, the bioadhesive contains about 0.1 to about 1 percent by weight of polymerized cross-linking agent.

A bioadhesive may be broadly defined as a material that adheres to a live or freshly killed biological surface such as mucus membrane or skin tissue. Bioadhesion as that phrase is used herein to define a useful bioadhesive is assayed by a procedure described hereinafter in Example 2 that measures the force required to separate two layers of freshly excised rabbit stomach tissue that are adhered together by an adhesive. Using this procedure, a bioadhesive may be defined as a material that requires a force of at least about 50 dynes/cm$^2$ to separate two adhered, freshly excised pieces of rabbit stomach tissue, following the procedure of Example 2. Upper limits for forces required to separate the freshly excised rabbit tissue are presently unknown, but are believed to be at least about 2000 dynes/cm$^2$.

For purposes of comparison, a non-bioadhesive, strongly acidic, macroreticular cross-linked and swellable polymer having sulfonic acid functionality such as the cation exchange resin sold by Rohm and Haas, Company of Philadelphia, Pa. as its AMBERLIT ® exchange resin requires almost no force to separate the excised tissue, while homopoly(2-hydroxyethyl methacrylate) requires a force of about 29 dynes/cm$^2$ for separation.

As noted previously, at least about 80 percent of the repeating units of the bioadhesive contain at least one carboxyl functionality. Exemplary monomers that provide these repeating units are monoethylenically unsaturated and include acrylic acid, methacrylic acid, fumaric acid, maleic acid, maleic anhydride which may be hydrolyzed into its acid form during or after polymerization, itaconic acid, crotonic acid, and the like. Each of these acids may be used alone or in combination with other such acids or with one or more pharmaceutically or cosmetically acceptable salts of those acids. Acrylic acid is a particularly preferred monomer for providing the repeating units of the bioadhesive polymer.

The bioadhesive polymers of this invention are cross-linked by cross-linking agents as are known in the art. The cross-linking agent is substantially free from polyalkenyl polyethers, and is particularly free from polyalkenyl polyethers such as polyallyl sucrose or polyallyl pentaerythritol containing an average of at least three allyl group molecules as are reportedly present in CARBOPOL ® 934. Exemplary of useful cross-linking agents are divinylbenze, N,N-diallylacrylamide, 3,4-dihydroxy-1,5-hexadiene, 2,5-dimethyl-1,5-hexadiene and the like.

The amount of cross-linking of the bioadhesive is of some import. When less than about 0.05 weight percent of an appropriate cross-linking agent is present, the bioadhesive tends to become water-soluble, or water-dispersible, thereby losing its desired water-insoluble, water-swellable, fibrous character that is important to the invention. When greater than about 1 percent cross-linking agent is present, the water-swellability of the bioadhesive begins to decrease appreciably. At cross-linking agent levels greater than about 1.5 percent, the water-swellability is sufficiently decreased so as to make the bioadhesive lose its desired, functional characteristics.

The above amounts of carboxy-functional repeating units and cross-linking agent are used to define the bioadhesive, but specifically refer to the percentages of those predecessor, unpolymerized monomers in the reaction mixture from which the bioadhesive is polymerized. These pre-polymerization amounts are utilized because of the great difficulty in analyzing the polymerized bioadhesive. Although the amounts refer to the pre-polymerized monomers, it is believed that the bioadhesives contain substantially similar amounts of those monomers in polymerized form.

A bioadhesive polymer useful herein may thus be defined as a reaction product of the copolymerization of at least 80 weight percent monoethylenically unsaturated carboxy-functional monomer and about 0.05 to about 1.5 weight percent of a cross-linking agent free of polyalkenyl polyether. The remaining monomers that may be present to constitute 100 percent by weight of the monomers are discussed below.

In addition to the above two ingredients, the bioadhesive polymer may also include polymerized monoethylenically unsaturated repeating units such as $C_1-C_6$ alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and tetraethylene glycol monoacrylate; methacrylamide, acrylamide and their $C_1-C_4$ mon- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The bioadhesive polymers most preferably are prepared from only the monoethylenically unsaturated carboxy-functional monomer and the cross-linking agent.

The bioadhesives useful herein may be prepared by conventional free radical polymerization techniques utilizing initiators such as benzoyl peroxide, azobisisobutyronitrile, and the like, are polymerized in an aqueous medium, and are not agglomerated by steam action. Exemplary preparations of useful bioadhesives are provided hereinafter and may also be found in U.S. Pat. No. 3,202,577, whose disclosures are incorporated herein by reference.

The polymers described in U.S. Pat. No. 3,202,577 are reported therein to be useful in treating diarrheal states. The disclosures of that patent are directed to the use of its polymers as bulking or dehydrating agents, and not as bioadhesives.

The bioadhesive useful herein is fibrous or particulate, and swellable in water, but is insoluble in water. Thus, the bioadhesive useful herein may be distinguished from those polymers of U.S. Pat. Nos. 3,074,852, 3,330,729 and 4,226,848, described hereinbefore that utilize CARBOPOL ® 934. That polymer does provide adhesion as discussed herein, but is water-soluble, making it less desirable, and is therefore excluded from the bioadhesives of this invention. Thus, CARBOPOL ® 934 is said in U.S. Pat. No. 4,226,848 to be sufficiently water-soluble to provide a measurable viscosity at a concentration of 0.2 percent by weight in water. Contrarily, as illustrated hereinafter in the examples, the bioadhesives useful herein are prepared in aqueous solution and separate therefrom after polymerization.

In addition, the polymers of U.S. Pat. Nos. 3,074,852, 3,330,729 and 4,226,848 are cross-linked by a polyalkenyl polyether such as the triallyl ether of sucrose or the triallyl ether of pentaerythritol. The bioadhesives of the present invention are substantially free of such cross-links, particularly of cross-links by agents having an average of at least about three allyl groups per molecule.

Nevertheless, the fibrous, bioadhesive polymers of this invention are swellable in water; i.e., the polymer particles sorb water (adsorb or absorb) and thereby become larger in size in the presence of water. The water used for that swelling, may be that provided along with the composition of the present invention or it may be that provided by the body of the treated animal, such as by gastric fluid or by mucosal secretions such as saliva.

The size of the bioadhesive particles has some effect upon the compositions of this invention. It is apparent that the bioadhesive particles should not be so large that the composition cannot be administered without undue difficulty. For example, if the composition is to be swallowed, the bioadhesive particles must be sized to permit passage of the composition to the stomach without impeding passage of subsequently ingested foods or liquids thereto. Similarly, when the composition is to be used in the eye, finely comminuted bioadhesive particles, e.g. sized to pass through a 100 mesh sieve screen (Tyler), are utilized so that visual impairment of the treated animal is minimized.

Typically, at the maximum, a useful bioadhesive is sized to pass through a sieve screen having a 10 mesh (Tyler); i.e., a 2000 micron opening. Preferably, the bioadhesive particles are sized to pass through a 30 mesh sieve screen (Tyler). Particles having a relatively small size swell more rapidly than do particles having a relatively large size, and thus, a relatively small size is preferred for the particles. Bioadhesion measurements discussed before and in Example 2 hereinafter are carried out using a bioadhesive sized to pass through a 30 mesh sieve screen and be retained on a 40 mesh sieve screen (Tyler).

Bioadhesion has not been found to be a function of the molecular weight of the bioadhesive. Consequently, the bioadhesive may be of substantially any molecular weight, so long as its adhesion in the adhesion test described hereinafter is at least about 50 dynes/cm$^2$.

As noted previously, the bioadhesives are polymerized in an aqueous medium. In preferred practice that aqueous medium is a saturated solution of an alkaline earth metal salt such as magnesium sulfate. The alkaline earth metal salt serves at least two functions. First, it increases the density of polymerization medium so that the polymerized bioadhesive floats on the surface of the aqueous medium and may be easily removed therefrom. Second, the use of magnesium sulfate, in particular, reduces the swelling of the bioadhesive in the aqueous medium so that polymerization and recovery are faciliated. Bioadhesives typically contain about 0.5 to about 1 percent of the alkaline earth metal ion after several water rinsings of the polymer.

A particularly preferred bioadhesive that is commerically available is that material sold under the designation polycarbophil by A. H. Robins Co. of Richmond, Va. *The United States Pharmacopeia*, 1980 edition, United States Pharmacopeial Convention, Inc., Rockville, Md., at page 638, indicates that polycarbophil is a polyacrylic acid cross-linked with a divinyl glycol that has a residue on ignition of less than 4.0% and absorbs about 60 times its original weight in test B under Absorbing power.

Useful bioadhesive polymers of this invention were examined as to their densities, which are typically about 1.30–1.70 grams/cubic centimeter (g/cc). The cross-linking percentage was found to have a small effect upon the resulting density of illustrative, synthesized polymers as is shown in the Table below. Also shown in that Table is a somewhat greater effect upon density that is observed for different starting monomers.

| Densities of Useful Bioadhesives | | | |
|---|---|---|---|
| Bioadhesive | | | Density[2] |
| Monomer | Cross-linker | %-CL[1] | (g/cc[3]) |
| acrylic acid | 3,4-dihydroxy-1,5-hexadiene | 0.05 | 1.49 |
| acrylic acid | 3,4-dihydroxy-1,5-hexadiene | 0.30 | 1.56 |
| acrylic acid | 3,4-dihydroxy-1,5-hexadiene | 0.60 | 1.57 |
| acrylic acid | 3,4-dihydroxy-1,5-hexadiene | 1.20 | 1.62 |
| acrylic acid | 3,4-dihydroxy-1,5-hexadiene | 2.00 | 1.65 |
| methacrylic acid | 2,5-dimethyl-1,5-hexadine | 0.3 | 1.47 |
| methacrylic acid | divinyl benzene | 0.3 | 1.36 |

[1]%-CL = weight percent cross-linking agent based upon total polymerizable monomers.
[2]Density of each polymer was determined in a 2 milliliter specific gravity bottle at 25° C. Benzene of known density (0.874 g/cc) was used at the medium.
[3]g/cc = grams per cubic centimeter.

The ratio by weight of bioadhesive to treating agent may be quite broad. Typically, the weight ratio of bioadhesive to treating agent is about 200,000:1 to about 1:100. In preferred practice, however, the weight ratio of bioadhesive to treating agent is about 1:10 to about 10:1. Those weight ratios are determined using dry ingredients.

In addition to the treating agent and bioadhesive, the compositions of this invention may also contain pharmaceutically or cosmetically acceptable diluents and/or one or more materials present as a medicinally inert matrix. For example, a useful bioadhesive may be coated on the surface of a pill containing the treating agent and appropriate diluents to form the pill and thereby form a composition of this invention. Exemplary compositions containing a medicinally inert matrix are discussed hereinafter. In addition, one or more lubricants, plasticizing agents, binders, vehicles, coloring agents, taste and/or smell controlling agents, and the like may also be present.

The phrases "pharmaceutically acceptable", "cosmetically acceptable", "physiologically tolerable" and "medicinally inert" are used herein to mean that the material so described may be used for treatments in or on humans or other mammals without causing ill effects, such as toxicity, blistering or whitening of mucosa or skin tissues, and that those materials are not themselves treating agents or bioadhesives, as those terms are used herein.

A composition of this invention may contain an intimate mixture of the bioadhesive and the treating agent. That intimate mixture may, for example, be a mixture of dry solids, or of the treating agent dissolved or suspended in a pharmaceutically or cosmetically acceptable (physiologically tolerable) carrier that also includes suspended particles of bioadhesive. The phrase "intimate mixture" is used herein to mean that the components of the composition are mixed substantially uniformly so that none of those components is localized. A minor amount of agitation immediately prior to use may be required for some liquid compositions of this invention to achieve an intimately mixed state when used.

Illustrative of an intimate mixture of dry composition components is an admixed powder formed from comminuted bioadhesive particles having a size sufficient to pass through a 40 mesh sieve screen and be retained on a 60 mesh sieve screen (Tyler) admixed with similarly or smaller sized particles of a treating agent such as chlorothiazide. (Hereinafter, when particles are sized to pass through one screen and be retained on a second screen, as above, the size of the passing screen mesh will be written first, followed by a virgule, "/", and then the size of the retaining screen mesh. Thus, the above passing and retaining screen mesh sizes are written "40/60".) The mixture may be provided for treatment in tablet form or within a gelatin capsule and ingested for treatment.

In another embodiment, the bioadhesive is swollen in an aqueous medium containing the treating agent, and the treating agent is sorbed (absorbed or adsorbed) into or onto the swollen bioadhesive particles. After drying, the composition so prepared is provided for treatment as described above. The word "dry" is used herein in relation to a bioadhesive to mean that the bioadhesive does not adhere when touched with a finger within a rubber glove, and is substantially unswollen.

A bioadhesive may also be employed with suppositories for rectal or vaginal administration. In such embodiments, the bioadhesive may be coated on the surface of a treating agent-containing suppository or it may be dispersed therein.

An aqueous dispersion of N,N-dimethylaminobenzoic acid and a bioadhesive is illustrative of one embodiment of this invention wherein the composition contains the bioadhesive and treating agent in an intimately mixed form in a cosmetically acceptable aqueous carrier.

In another illustrative embodiment, the treating agent and bioadhesive are intimately mixed in an pharmaceutically acceptable aqueous carrier and may be used in eye. Here, the treating agent such as the sparingly soluble anti-inflammatory agent fluorometholone is provided as a saturated solute in a pharmaceutically acceptable aqueous carrier. The bioadhesive comminuted to a 40/60 mesh sieve screen size, and more preferably to pass through a 100 mesh sieve screen (Tyler) is added to the saturated fluorometholone solution to form a composition of this invention. The composition so prepared may then be instilled in the precorneal pocket of the eye to contact the conjunctival surface, and thereby provide contact of the controlled release treating composition to that mucus membrane.

The bioadhesive provides the dose rate-controlling medium of the above compositions. In more preferred embodiments, the rate of controlled release is provided primarily by a medicinally inert matrix, such as a polymer, that is also present in the composition. A composition of this invention that contains a treating agent in such a matrix may be in the form of a three-dimensional structure such as a film, a laminate, a microcapsule or aggregate of microcapsules, each of which structures has at least one surface portion on which the bioadhesive is disposed. Such more preferred embodiments are discussed hereinbelow.

Reference is made in the following discussion to embodiments of this invention illustrated in FIGS. 3 through 8. Identical or functionally analogous elements shown in those figures are designated by identical reference numerals followed by a capital letter. One capital letter is used throughout each figure, except for FIGS. 5 and 6 wherein the same capital letters are used.

It is to be noted that the figures discussed hereinbelow are not drawn to scale. As a consequence, the thicknesses of an illustrated film or laminate layer, or a dimension of a bioadhesive particle or capsule are not intended to represent the relative thicknesses or dimensions of those materials. Similarly, the number of bioadhesive particles and of capsules illustrated in each figure are intended as exemplary and may not represent the actual relative numbers of such materials in a structure.

For purposes of clarity, the treating agent 14 is illustrated in FIGS. 3 through 8 as discrete dots. It is to be understood, however, that the treating agent may be dissolved in the matrix and thus not visible, or it may be suspended in the matrix as an insoluble solute, or it may be partly dissolved and partly suspended in the matrix.

FIG. 3 illustrates an embodiment of this invention in the form of a film and is designated generally by the reference numeral 10. The film 10 contains a first medicinally inert matrix 12A that contains the treating agent 14A. The film 10 defines at least one surface portion 16A, and as shown, also defines a second surface portion 18A. The bioadhesive 20A is disposed on at least the first surface portion 16A, and a second amount of bioadhesive may also be disposed on the second surface portion 18A.

FIG. 4 illustrates another embodiment of this invention wherein the composition is in the form of a laminate generally designated by the reference numeral 100. In this embodiment, a first layer of the laminate 12B comprising a first medicinally inert matrix contains the treating agent 14B and defines a first surface 17B and a second surface 19B.

A second layer of the laminate 22B is comprised of a second medicinally inert matrix, and defines a first surface 16B and a second surface 15B. The second layer 22B is adhered t the first surface 17B of the first layer 12B along the second surface 15B. The first surface 16B of the second layer 22B also defines the first surface portion of the laminate on which the bioadhesive 20B is disposed.

The embodiment 100 illustrated in FIG. 4 further includes a third layer 24B comprising a third medicinally inert matrix and defining a first surface 23B and a second surface 25B. The first surface 23B of the third layer is adhered to the second surface 19B of the first layer 12B. The second surface 18B of the third layer 24B also defines a second surface portion (18B) of the three-dimensional structure (laminate). As illustrated, the second surface portion 18B of the laminate 100 also contains a bioadhesive 21B disposed thereon.

Another embodiment of this invention is illustrated by the first and second layers of the laminate 100 of FIG. 4. In that embodiment, the third layer 24B is absent and a second surface portion of the laminate, otherwise designated by the reference numeral 18B, is defined by the second surface 19B of the first layer 12B.

Still further embodiments of the invention may also be illustrated with reference to FIG. 4. In one such embodiment, the three-layered laminate is present as shown, but a bioadhesive is disposed on only the first surface portion 16B of the laminate; i.e., the bioadhesive 21B disposed on the second surface 18B of the laminate is absent. In still another embodiment, the two-layered laminate discussed in the paragraph immediately above is provided with a bioadhesive 21B disposed additionally on the second surface portion of the laminate.

Another embodiment of the invention is illustrated in cross-section in FIG. 6 and is generally designated by the reference numeral 200. In this embodiment, the composition has a capsular, three-dimensional form. Here, a medicinally inert matrix 12C contains the treating agent 14C. The medicinally inert matrix 12C defines a first surface portion 16C of the capsule on which a bioadhesive 20C is disposed.

The capsules disclosed herein typically have an average largest dimension of about 1 nanometer to about 5000 microns. As such, those capsules having an average largest dimension of about 1 to about 999 nanometers are referred to as nanocapsules, while capsules having an average largest dimension of about 1 micron (1000 nanometers) to about 5000 microns are referred to as microcapsules. Nanocapsules may be prepared by following the teachings of Kreuter, *Pharm. Acta Helv.*, 58, 196 (1983). The microcapsules typically have an average largest dimension of about 50 to about 2500 microns, while nanocapules have typical average largest dimensions of about 50 to about 800 nanometers.

FIG. 5 illustrates an alternative form of the capsules 200 of FIG. 6, wherein a plurality of capsules 200 are adhered together to form a capsule aggregate generally designated by the reference numeral 200a. The capsule aggregate 200a is typically held together by the adhesion provided by the bioadhesive particles. The aggregate may be comprised of a single type of capsule that contains a single treating agent, or of a plurality of different types of capsules that contain one or more treating agents.

Due to the relative ease or preparation of capsule aggregate compositions 200a as compared to individual capsule compositions 200, capsule aggregate compositions 200a are typically utilized herein. Capsules comprised of a medicinally inert matrix surrounding a treating agent, but lacking bioadhesive particles are also useful herein in additional embodiments of the invention as is discussed hereinbelow.

In a film embodiment, such as that illustrated in FIG. 7 and designated generally therein by the reference numeral 300, the treating agent 14D is contained within capsules 26D similar to those of FIG. 6 designated by the reference numeral 200, but lacking a bioadhesive analogous to the bioadhesive 20C of FIG. 6. The capsules 26D of the embodiment of FIG. 7 are themselves contained in a film comprised of a first medicinally inert matrix 12D. The first matrix 12D defines at least a first surface portion 16D of the film, and as shown, defines a second surface portion 18D.

The bioadhesive 20D of this embodiment is disposed upon the first surface portion 16D. Of course, if desired, bioadhesive may also be disposed upon the second surface portion 18D defined by the first matrix 12D of film 300.

The laminate illustrated in FIG. 8 and designated therein generally by the reference numeral 400 is analogous to the laminate 100 of FIG. 4, with the exception that the treating agent 14E is contained in capsules 26E that are themselves contained in the first medicinally inert matrix 12E. It is to be understood that further embodiments of the invention analogous to the two- and three-layered further embodiments discussed in relation to FIG. 4 are also contemplated wherein a treating agent analogous to agent 14E is contained in capsules analogous to the capsules 26E of FIG. 8.

It is to be noted that a laminate of this invention is not intended to be limited to a structure having two or three layers. Rather, the laminate may contain about five or more layers. In addition, the laminate may include more than one layer that contains a treating agent. The figures and the previous description illustrate and describe relatively simple laminates for purposes of easy understanding. It is to be understood, however, that more complex, multi-layered structures that embody the concepts illustrated and described herein are also contemplated.

For example, in yet another embodiment (not shown), a plurality of layers of medicinally inert matrix, at least one of which contains a treating agent, may be prepared into a relatively thick laminate. The laminate so prepared may then be sliced into thin slices, as with a microtome, such that the principal surfaces of the laminate are the cross-sectional surfaces. A bioadhesive may then be adhered to such a cross-sectional surface to prepare a composition of this invention as individual particles or as a particle aggregate. Such a laminate, prior to the addition of bioadhesive, has an appearance similar to the cross-sectional view of a multi-layered cake.

A laminate of this invention is thus seen to define at least one surface portion on which a bioadhesive is disposed. That laminate contains a plurality of medicinally inert matrices in layers, each of which layers defines a first surface and a second surface wherein the layer surfaces are in stacked relation, with surfaces of adjacent layers being adhered together. At least one of the medicinally inert matrix layers contains an effective amount of a treating agent, and a surface of one of those layers defines the at least one surface portion of the laminate on which the bioadhesive is disposed.

It is also to be noted that the capsules, films and laminates discussed and illustrated herein need not be monolithic, having a continuous surface. Rather, if desired, a capsule, film and/or laminate of this invention may be foraminous and be pierced with a plurality of holes as to provide relatively more rapid release of the treating agent. Such holes or pores are usually present in the microcapsules described in the examples, and may extend through the three-dimensional structure, or may extend only part way through or within such a structure.

The medicinally inert matrices discussed hereinbefore may be made from materials that are chemically the same or different. The chemical identity of the medicinally inert matrix of any layer or film is dependent upon the controlled treating agent release that is desired, as is known.

Exemplary useful medicinally inert matrices include cross-linked human serum albumin or bovine serum albumin (BSA); cross-linked gelatin; poly(2-hydroxyethyl methacrylate) (hereinafter denominated p-HEMA); copolymers containing HEMA and monoethylenically unsaturated monomers such as those described hereinbefore as useful in the preparation of bioadhesives and some of which are described in U.S. Pat. No. 4,028,295; $C_1$-$C_4$ alkyl cellulose ethers and cellulose ethers containing substituted $C_1$-$C_4$ alkyl groups such as ethyl cellulose and hydroxypropylmethylcellulose, respectively; ethylene-vinyl acetate copolymers as are described in U.S. Pat. No. 4,166,111; ethylene:propylene:diene copolymers as are described in U.S. Pat. No. 3,590,119; cross-linked elastomers as described in U.S. Pat. Nos. 3,639,583 and 3,417,181, and the like.

The above-mentioned matrices typically provide the principal rate-controlling means of release of the treating agent. That release may be obtained by gradual dissolution of the matrix or by erosion of the matrix through a dispersion mechanism to thereby provide a fresh supply of treating agent to the site of treatment, or by leaching of the treating agent from the matrix in the presence of water provided by the treated animal. Many systems providing release of active ingredients from a matrix over a period of time are themselves known, and such known systems in themselves are not a part of this invention. Rather, it is the combination of such systems with a bioadhesive described herein to provide an improved controlled release composition that forms a part of this invention.

The medicinally inert matrices comprising the films and laminate layers described in relation to FIGS. 3-8 may each have a thickness in those structures of about 50 to about 3000 microns, and more preferably of about 100 to about 1500 microns. Where multiple layers of matrices are utilized it is preferred that each layer be less than about 1000 microns thick, but those layers may provide a laminate having a thickness of greater than about 1000 microns. Where single matrix films are used, the thickness of such films is typically about 500 to about 1000 microns, although thicker films up to about 3000 microns are also useful.

The various adjacent layers of the beforedescribed laminates may be adhered to each other by the adhesive character provided by each layer to its adjacent neighbor. For example, the surfaces of adjacent layers may be wet with solvent and then placed together so that the matrices interdissolve or interdisperse to provide the adherence. The adjacent layers of the laminate may also be adhered together by means of a separate layer of adhesive placed therebetween.

The bioadhesive particles disposed upon at least one surface portion of the beforedescribed three-dimensional structures typically adhere to those surfaces through their own adhesive properties, and are typically disposed upon that at least one surface portion in a wet, swollen, adhesive form. Wetting of the surface portion on which the bioadhesive particles are disposed softens many useful matrices and permits at least partial entrapment of the bioadhesive particles in the softened surface.

A method of controlled release treatment also constitutes an aspect of this invention. In accordance with this method, a controlled release composition containing an effective amount of treating agent per dose is provided, as described before. An area of skin or mucus membrane to be treated is contacted with the provided composition. The contact is carried out in the presence of sufficient water to swell the bioadhesive and cause the bioadhesive-containing composition to adhere to the area contacted, as well as cause the controlled release of the treating agent in the vicinity of that contact.

The compositions of this invention may provide the intimate contact between the treating agent and the mucosa that is preferred for high molecular weight treating agents such as proteins and hormones. These compositions, through their bioadhesion, maintain the intimate contact for extended periods of time to thereby increase the relative concentration of the treating agent in the vicinity of that contact.

Each of the beforedescribed compositions may be administered in accordance with this method.

The compositions of this invention may be administered by several means to provide the desired contact between the skin or mucus membrane and the composition. For example, where the treating agent is a sun screen, the composition may be applied to the skin by rubbing the composition over the skin area to be treated. Where the conjunctival mucosa are to be contacted, the aqueous composition described above may be instilled into the precorneal pockets of the eyes. Where the buccal, nasal, anal and/or vaginal mucosa are to be contacted, the composition may be applied by hand, forceps or other suitable instrument. Where the mucosa of the stomach and/or intestines are to be contacted, the composition is typically swallowed, or implanted surgically, and contact with the mucus membrane is achieved by the contraction of the stomach or intestines and/or by the carrying action provided by passage of gastric fluids therethrough.

The composition is left in place (contact maintained) for a time sufficient for the treating agent to be released over a controlled period, and thereby provide its medicinal or cosmetic function to the treated animal. In most circumstances, some unused, still active, controlled release composition and the remainder of the composition administered are eliminated from the body by a natural bodily mechanism, such as by dispersion or erosion caused by an aqueous body fluid such as saliva, tears, gastric fluid or vaginal secretions. In other instances, such as where the treating agent is contained in a medicinally inert matrix such as an ethylene-vinyl acetate copolymer or cross-linked elastomer that is ingested, the flushing action provided by the flow of gastric fluids and stomach contractions ultimately results in excretion in the feces of any unused composition and of the remainder of the administered composition.

BEST MODES FOR CARRYING OUT THE INVENTION

EXAMPLE 1

Bioadhesive Polymer Preparation

Bioadhesive polymers useful herein were prepared following the general synthetic procedure discussed immediately below. Specific bioadhesive polymers made in accordance with the general procedure are illustrated in Table 1, hereinafter.

A solution containing 100 milliliters of distilled water and 800 grams of magnesium sulfate ($MgSO_4 \cdot 7H_2O$) was heated to reflux with agitation. A mixture of 1 gram of initiator dissolved in 100 grams of monomeric carboxy-functional repeating unit and the amount of cross-linking agent shown in Table 1 was added to the refluxing aqueous solution with continued stirring. The polymerizing composition so prepared was agitated and heated to the temperature shown in Table 1 for the period of initial polymerization and of post-polymerization curing.

At the termination of the curing time, the polymerized composition was diluted with 150 milliliters of distilled water heated to a temperature of about 95° C. and then strained through a stainless steel sieve having a 40 mesh screen (Tyler). The strained bioadhesive remaining on the screen was washed with one 1 liter portion of water heated to a temperature of about 80° C. followed by five separate 1 liter washings using tepid water. The washed bioadhesive so prepared was then dried in a forced air oven at a temperature of 90° C. for a period of 48 hours.

The bioadhesives so prepared were then used as such or comminuted and sieved to provide a desired particle size.

TABLE 1

| Bioadhesives | | | | | | |
|---|---|---|---|---|---|---|
| | Cross- | | Polymerization Conditions | | | |
| Carboxyfunctional Repeating Unit[1] | Linking Agent[2] | Initiator[3] | Poly. Time[4] | T.[5] | Time[6] | Yield[7] |
| (A) | (a) 0.2 | (1) | 15 | 95 | 2 | 83 |
| (A) | (b) 1.0 | (1) | 25 | 95 | 18 | 67 |
| (B) | (a) 1.0 | (1) | 30 | 95 | 48 | 53 |
| (B) | (b) 1.0 | (1) | 30 | 95 | 48 | 87 |
| (C)[8] | (a) 1.0 | (1) | — | 65 | 24 | 11 |
| (D)[8] | (a) 0.2 | (2) | 20 | 95 | 72 | 10 |
| (A) | (c) 0.2 | (1) | 10 | 95 | 4 | 98 |
| (B) | (c) 0.2 | (1) | 10 | 95 | 20 | 93 |

[1] 100 Grams of each of the following carboxy-functional repeating units was used:
(A) = acrylic acid;
(B) = methacrylic acid;
(C) = itaconic acid; and
(D) = maleic anhydride.
[2] The numerals of the Table indicate the number of grams of the particular cross-linking agent used. The particular cross-linking agents were:
(a) = 3,4-dihydroxy-1,5-hexadiene;
(b) = divinyl benzene; and
(c) = 2,5-dimethyl-1,5-hexadiene.
[3] One gram of the following initiators was used:
(1) = benzoyl peroxide; and
(2) = azobisisobutyronitrile.
[4] Initial polymerization time in minutes.
[5] Temperature in degrees C. for initial polymerization and post-polymerization cure.
[6] Post-polymerization cure time in hours.
[7] Yield of dried bioadhesive based upon the weights of starting materials and recovered bioadhesive.
[8] A nitrogen sparge was used during polymerization as was deaerated distilled water prepared by boiling distilled water for a period of 10 minutes.

Although optimization of polymerization conditions not reflected in the data of Table 1, it can be seen from those data that the bioadhesives useful herein are easily prepared in useful quantities. It is noted that the first bioadhesive listed in Table 1 has bioadhesion and other physical and chemical properties that are substantially identical to the commercially available bioadhesive sold under the designation polycarbophil by by A. H. Robins Co. of Richmond, Va.

EXAMPLE 2

Measurement of Adhesion

As noted previously, a bioadhesive of this invention is a water-insoluble, but water-swellable, fibrous, cross-linked carboxy-functional polymer that contains specified amounts of carboxyl functionality and cross-linking agent. In addition, to that chemical definition, a useful bioadhesive by definition must also exhibit an adhesion between two pieces of freshly excised rabbit stomach tissue of at least about 50 dynes/cm$^2$ when measured under specified conditions. Those conditions and the apparatus utilized for that measurement are described hereinbelow.

The apparatus utilized for these measurements is illustrated in FIG. 1. Basically, the apparatus is a standard, surface tensiometer as is available from Biolar Corporation, of North Grafton, Mass. that has been modified by removal of the du Nuoy loop and its replacement by an elongated linking arm 48 and an excised stomach tissue holding means 44.

Fresh stomach was obtained from rabbits and was carefully washed with a solution containing 0.9 weight percent sodium chloride in distilled water (saline solution) to remove the contents. The stomach was placed in an aerated saline solution until used.

The tissue was cut into a round shape from the fundus part of the stomach and secured mucosal side out over a weighted container such as a 15 milliliter scintillation vial using a rubber band, as indicated by the reference numeral 40 of FIG. 1. The container 40 was placed into a 500 milliliter beaker 42 containing gastric fluid. The beaker 42 was placed under the scale portion of the modified tensiometer as illustrated in FIG. 1.

A separate portion of excised stomach tissue was separated into two layers of smooth muscle; i.e., the external longitudinal layer and the internal circular layer. A piece of the internal circular layer was placed mucosal side out over a No. 2 rubber stopper, and the tissue was secured to the rubber stopper using an aluminum vial cap having a uniform-sized opening of about 0.78 square centimeters. The aluminum vial cap is available from Wheaton Company of Millville, N.J. A holding means in the form of screw eye was inserted into the opposite end of the rubber stopper from that to which the tissue was secured. The rubber stopper containing the holding means and affixed tissue was placed in an aerated saline solution until used.

One hundred microliters of gastric fluid was added to 4 milligram samples of each polymer whose bioadhesion was to be measured. One hour after that addition, the swollen polymer was carefully spread over the tissue on the rubber stopper. Any excess of fluid was removed from the polymer by blotting with a tissue paper. The rubber stopper with holding means, tissue and polymer 44 was suspended from the scale so that it rested in the beaker of gastric fluid. When the polymer layer was at a depth equal to that of the tissue already in the container on vial 40, the scale was adjusted to zero using appropriate weights. The rubber stopper with holding means, tissue and polymer 44 was then suspended over the tissue on the weighted container 40, and that container 40 was elevated to contact the polymer using the elevation means 46. Care was taken to assure that the tissue on the container 40 touched only the polymer.

The beaker was then slowly raised until the tissues came into contact, the contact being initiated by the weight of the rubber stopper (1.8 grams). After one minute, the weight was removed, and the force required to separate the polymer from the tissue was measured. The force exerted to separate the layers of stomach tissue was increased at a constant rate of 10 milligrams per second in weight until the tissues separated.

One measurement was carried out within five minutes of contact between the tissue and adhesive of rubber stopper 44 and the tissue of the vial 40. Excised stomach tissue was affixed to either the vial or rubber stopper within 30 minutes of sacrificing the rabbit and is thereby considered to be freshly excised tissue.

Exemplary results using the above measurement technique are illustrated for four useful bioadhesives in Table 2 hereinafter. The bioadhesives were prepared as described in Example 1 with the exception that 0.3 weight percent of cross-linking agent was utilized. After the preparation, the bioadhesives were sieved and particles having a 30/40 mesh size (Tyler) were used for these measurements.

TABLE 2

| Polymer[1] | Bioadhesion Measurements | | Number of Measurements |
|---|---|---|---|
| | Weight to Separate Tissues[2] | Force to Separate Tissues[3] | |
| 1 | 855 ± 55 | 1061 ± 68 | 13 |
| 2 | 864 ± 56 | 1072 ± 68 | 12 |
| 3 | 876 ± 57 | 1086 ± 71 | 13 |
| 4 | 306 ± 45 | 380 ± 56 | 8 |

[1]Polymer 1 = polyacrylic acid cross-linked with 3,4-dihydroxy-1,5-hexadiene; polymer 2 = polyacrylic acid cross-linked with 2,5-dimethyl-1,5-hexadiene; polymer 3 = polyacrylic acid cross-linked with divinylbenzene; and polymer 4 = polymethacrylic acid cross-linked with divinylbenzene.
[2]Weights are in milligrams ± standard error of the mean (S.E.M.)
[3]Forces are reported in dynes/cm$^2$ ± S.E.M.

Using the above measuring technique, p-HEMA commercially available from Aldrich Chemical Co. of Milwaukee, Wis., required a force of 29 dynes/cm$^2$ to separate the tissues, while AMBERLITE ® 200 cationic exchange resin available from Rohm and Haas Co. of Philadelphia, Pa., required almost no force to separate the tissues.

EXAMPLE 3

Gastrointestinal Transit of a Bioadhesive

The following study illustrates the adhesion of a typical bioadhesive to the mucosa of the gastrointestinal tract of the rat. Chromium ions have been found to bind to the bioadhesives and are not substantially absorbed across biological membranes. Thus, radioactive chromium ions ($^{51}$Cr) were a convenient tag for the presence of the bioadhesive.

Commercially available polycarbophil, density=1.56 g/cc, (10 grams, 30/40 mesh) was swollen in distilled water (50 milliliters) to which was added $^{51}$ chromic chloride (1 milliCurie). The resulting admixture was agitated for a period of 24 hours.

The suspension was filtered, and the swollen bioadhesive was resuspended in 600 milliliters of distilled water, stirred for several hours and filtered again. The swollen bioadhesive was then suspended in gastric fluid without pepsin (pH 1.2, U.S.P.), stirred and filtered repeatedly until no radioactivity was detected in the washing filtrate.

The $^{51}$Cr-labeled bioadhesive so prepared was dried for 24 hours in a hot air oven and then sieved again to provide 30/40 mesh (U.S. Standard Sieve Series) particles.

150 Milligrams of the $^{51}$Cr-labeled bioadhesive were packed into No. 3 hard gelatin capsules (Parke-Davis Division of Warner-Lambert Company, Morris Plains, N.J.). The radioactivity of each capsule was measured immediately prior to administration using an Auto-Gamma Scintillation Spectrometer model No. 5236 (Hewlett-Packard Co., Palo Alto, Calif.).

Male Sprague-Dawley rats weighing between 150 and 200 grams each were fasted for 48 hours, with free access to water, prior to administration. Each animal was anesthetized by placing it into a covered vessel having a gauze pad saturated with ether (Anesthetic grade, Mallinckrodt, Inc. Paris, Ky.) attached to its inside surface. The animal was kept in the chamber for about three minutes, promptly removed, and secured on a surgical board with adhesive tape in the supine position after trimming its abdomimal hair with animal clippers. The peritoneum was opened with a longitudinal incision about two centimeters in length.

The stomach was located and carefully removed intact from abdominal cavity with a forceps, and an opening two to three millimeters in diameter was cut into the fundus with surgical scissors. A prepared gelatin capsule containing $Cr^{51}$-labeled polycarbophil was placed in the stomach through the opening so made.

The opening was then tied shut with a loop of sutures [3-0 silk (2 metric) silicone treated nonabsorbable surgical sutures, U.S.P. Davis and Geck, Inc. Manati, PR], and tied in a square knot.

The stomach was replaced into the abdominal cavity and four milliliters of normal saline was injected into it using 27½ G needle. The external incision was closed with three or four sutures made with an eye needle (stainless steel, 706-1 eye needle, ⅜ circle, cut edge; The Terrington Co., Terrington, Conn.) in both the peritoneum and epidermis.

The animal was placed in a cage and allowed to recover.

The procedure was done in about five minutes. Anesthesia was maintained as needed by using a 50 milliliter beaker containing an ether-moistened gauze pad placed over the nose of the rat.

After a predetermined time period, each rat was removed from its cage, placed into the ether chamber for anesthesia, and sacrificed. The peritoneal cavity was opened and the stomach was carefully removed after clamping both of the cardiac and pyrolic junctions of the stomach. The excised stomach was carefully placed in the bottom of a gamma scintillation counting vial (15×30 millimeters, Packard test tubes for gamma counting Model #6001122).

The radioactivity of the counting vial containing a stomach was measured using the above Gamma scintillation counter.

Table 3, below, shows the amount of $^{51}$Cr-labeled bioadhesive remaining in the rat stomachs at various times after insertion of the gelatin capsules. It can be seen that the bioadhesive remains in the stomach for a period of about 17–24 hours.

TABLE 3

| | Retention of Bioadhesive in Rat Stomachs | |
|---|---|---|
| Time[1] | Number of Rats | Percent of Bioadhesive Retained in the Stomachs[2] |
| 1 | 6 | 96.86 ± 1.15[a] |
| 2 | 5 | 91.30 ± 2.52 |
| 4 | 5 | 84.79 ± 2.42 |
| 6 | 4 | 78.31 ± 1.50 |
| 10 | 5 | 54.60 ± 1.00 |
| 17 | 5 | 37.00 ± 3.40 |
| 24 | 5 | 9.00 ± 3.20 |

[1]Time in hours after insertion of gelatin capsules.
[2]Percent ± S.E.M.
[a]mean ± standard error of the mean.

1 Time in hours after insertion of gelatin capsules.
2 Percent±S.E.M.
a mean±standard error of the mean.

A repeated, similar study showed similar results for retention of the $^{51}$Cr-labeled bioadhesive in the stomach. In that study, the small intestines of the rats were also excised and cut into 20 approximately equal lengths. The radioactivity remaining in each of those lengths of intestine was then counted following the above-discussed procedures.

The results from the study of retention of the bioahdesive in each of the 20 segments of the small intestine are shown graphically in FIG. 2 from left to right in the direction from stomach toward the colon. The total percentage of the administered bioadhesive present in the small intestine is shown by the numerals above each graph. The areas under each portion of the graph are proportional to the amount of bioadhesive in that segment of small intestine. Examination of the graph shows the change in distribution from the stomach-end of the intestine toward the colon-end.

Another, similar, stomach-emptying determination was conducted using a bioadhesive prepared from methacrylic acid cross-linked with divinylbenzene, density=1.36 g/cc, and shown as Polymer 4 of Table 2. The results of that determination are shown below in Table 4.

TABLE 4

| | Retention of Bioadhesive in Rat Stomachs | |
|---|---|---|
| Time[1] | Number of Rats | Percent of Bioadhesive Retained in the Stomachs[2] |
| 2 | 5 | 82.25 ± 3.79 |
| 4 | 7 | 65.71 ± 4.96 |
| 6 | 7 | 62.50 ± 3.91 |
| 8 | 5 | 33.89 ± 5.55 |
| 16 | 5 | 8.28 ± 2.74 |

[1]Time in hours after insertion of gelatin capsules.
[2]Percent ± S.E.M.

As can be seen from a comparison of the data in Tables 3 and 4, and the data in Table 2, the methacrylic acid-divinylbenzene bioadhesive is less adherent to the stomach mucosa than is polycarbophil or a bioadhesive with similar adhesion properties to polycarbophil. Nevertheless, the data for the control determinations discussed hereinbelow illustrate that both bioadhesives provide a substantial improvement in the time required for the stomach to empty its contents.

In one control determination, 1 milliCurie of $^{51}$chromic chloride was added to 50 milliliters of normal saline solution and mixed thoroughly. Four milliliters of that mixture were injected into the stomachs of rats following the surgical procedure described before.

The radioactivity contained in each solution was measured prior to administration. The rats were sacrificed after selected time periods, and the amount of radioactive solution remaining in the stomachs isolated from those rats was determined using the above scintillation counter. The results of this determination are shown in Table 5, below, as the percentage of originally injected $^{51}$chromic chloride solution remaining in those stomachs.

TABLE 5

| | Amount of $^{51}$Cr-Normal Saline Solution Remaining in Rat Stomachs | |
|---|---|---|
| Time[1] | Number of Rats | Percent of $^{51}$Cr-Normal Saline Retained in the Stomachs[2] |
| 5 | 5 | 37.3 ± 4.40 |
| 10 | 5 | 26.6 ± 5.10 |
| 20 | 5 | 20.3 ± 2.50 |
| 30 | 5 | 14.7 ± 1.50 |
| 60 | 5 | 5.0 ± 0.90 |

[1]Time in minutes after injection.
[2]Percent ± S.E.M.

Cationic exchange resin beads were used as exemplary of non-bioadhesive-containing microcapsules to determine the time required for such microcapsules to be emptied from the stomach.

AMBERLITE®200 exchange resin beads, density=1.53 g/cc were sieved to provide 30/40 mesh (Tyler) particles. 150 Milligrams of the beads were packed into clear, hard gelatin capsules after counting the number of beads in each capsules. Approximately 2880 beads were contained in each capsule.

The gelatin capsules so prepared were surgically implanted into rat stomachs as described previously. The animals were sacrificed at various times after implantation as described, and the stomachs were carefully removed and opened with a surgical scissors. The beads present in each stomach were then counted. The results of this determination, expressed as a percentage of the number of beads implanted per animal, are shown in Table 6, below.

TABLE 6

| | Amount of Exchange Resin Beads Remaining in Rat Stomachs | |
|---|---|---|
| Time[1] | Number of Rats | Percent of Beads Retained in Stomachs[2] |
| 1 | 5 | 95.80 ± 1.90 |
| 2 | 6 | 62.40 ± 3.30 |
| 3 | 4 | 26.75 ± 5.40 |
| 4 | 4 | 11.80 ± 3.50 |
| 6 | 5 | 3.60 ± 1.20 |
| 8 | 5 | 3.80 ± 1.20 |

[1]Time in hours after insertion of gelatin capsules.
[2]Percent ± S.E.M.

Figure 11:
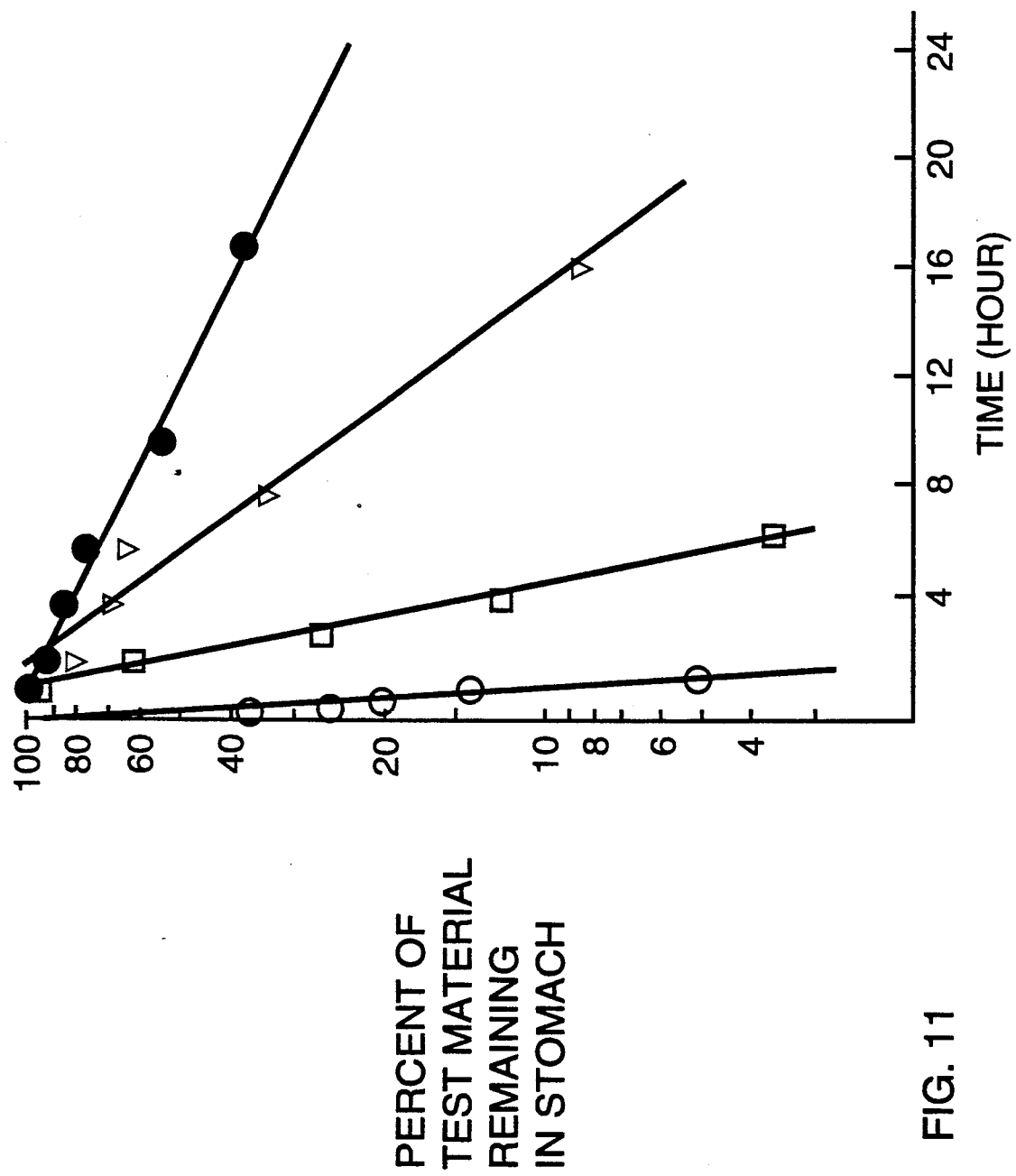
FIG. 11 is a semilogarithmic plot showing of the percentage of radiolabeled materials studied remaining in rat stomach versus time. Closed circles (●) represent $^{51}$Cr-labeled poly(acrylic acid/0.3 weight percent 3,4-dihydroxy-1,5-hexadiene); density=1.56 g/cc; y=2.025−0.027x (r=−0.9937). Inverted triangles (▽) represent $^{51}$Cr-labeled poly(methacrylic acid/0.3 weight percent divinyl benzene); density=1.36 g/cc; y=2.138−0.0745x (r=−0.9850). Open squares (□) represent AMBERLITE® resin beads; density=1.53 g/cc; y=2.130−0.296x (r=−0.9960). Open circles (○) represent $^{51}$Cr-normal saline; y=1.616−0.015x (r=−0.9971).

It can thus be seen from the above data, and the data of FIGS. 2 and 11 that illustrate intestinal transit of bioadhesive and stomach retention of bioadhesive and controls, respectively, that the bioadhesives useful herein are particularly adherent to the stomach and intestinal mucosa. These data also suggest that compositions containing these bioadhesives and a treating agent as described herein are also similarly adherent.

EXAMPLE 4

Bioadhesive-Coated Bovine Serum Albumin Microcapsules

The diuretic and anti-hypertensive drug chlorothiazide suffers from the disadvantage of being poorly sorbed from the gastrointestinal tract and into the blood stream. As a consequence of its relatively low sorption, much of the dosage administered orally, by pill, is excreted prior to the treating agent being sorbed and used by the body. This drug is therefore frequently prescribed to be taken more than once per day. It would therefore be beneficial if the effect of a single dose could be prolonged and if a greater percentage of the treating agent per dose could be sorbed.

Microcapsules containing chlorothiazide [6-chloro-2H-1,2,4-benzothiadiazine-7-sulfonamide 1,1-dioxide (1)] and having a surface coating of a bioadhesive useful herein were prepared as a composition of this invention. The procedures of Lee et al., *Science*, 213, 233 (1981) and Royer et al., *J. Parenter. Sci. Technol.*, 37, 34 (1983) were followed in modified form for this preparation.

Two hundred milligrams of bovine serum albumin (fraction V, powder; Sigma Chemical Co., St. Louis, Mo.) (BSA) were dissolved in each of six test tubes, each tube containing of 1 millimolar phosphate buffer (pH 7.5) at a temperature of 0°–4° C. 100 Milligrams of chlorothiazide (lot #L311,040-00N55; Merck Sharp & Dohme Research Laboratories, Rahway, N.J.) was then suspended in each albumin solution. Cross-linking of the BSA was initiated by the addition of 160 microliters of a 25 percent by volume solution of glutaraldehyde (Grade II, Sigma Chemical Co.) of each suspension. This resulted in a final glutaraldehyde concentration of 4 percent by volume in each solution.

Each suspension so prepared was agitated by vortex mixing, and the contents of each test tube were separately and immediately injected into a stirred oil phase using a 1 milliliter syringe fitted with a 20G needle. The oil phase consisted of 110 milliliters of petroleum ether, 90 milliliters of $CCl_4$ and 1 gram of sorbitan monoleate and was stirred at a rate of 120 revolutions per minute (rpm). Stirring was continued for about one hour after which time the microcapsules so produced were washed 3 times with 50 milliliter portions of petroleum ether, dried in a vaccum dessicator for about 16 hours and then sieved to provide a fraction having a 10/20 mesh size (U.S. Standard Sieve Series); i.e., about 840 to about 2000 microns in largest dimension.

Equal masses of the microcapsules so prepared and polycarbophil [sieved to provide an 80/100 mesh Tyler sized particles] were provided. The polycarbophil was allowed to swell in an excess of deaerated distilled water (Example 1). After swelling, the microcapsules were added to the swollen bioadhesive and the admixture so prepared was mixed thoroughly by hand. The resulting mixture was poured onto an aluminum dish and dried in an oven at a temperature of 70° C. for several hours.

The dry, hardened mass was scraped off of the dish with a spatula. The bioadhesive-coated microcapsules and aggregates thereof so produced and constituting compositions of this invention were of variously sized particles. Those particles were then loaded into No. 3 gelatin capsules for use in oral administration or administration by surgical implacement into the stomachs of animals.

As far as can be determined, substantially all of the chlorothiazide, BSA and polycarbophil were contained in the ultimately produced composition. Thus, the ratio by weight of bioadhesive to treating agent in this composition was about 3:1 (1 part treating agent+2 parts BSA+3 parts bioadhesive).

EXAMPLE 5

Bioadhesive Coated Gelatin Microcapsules

128 Grams of distilled water at a temperature of about 55°–60° C. were admixed with agitation with 38 grams of gelatin. After standing at room temperature for 24 hours, the gelatin had dissolved (swollen) completely to form a solution. The gelatin solution was then refrigerated at a temperature of about 2°–5° C. for a further 24 hour period.

The hard gel resulting from the refrigeration step was cut into small cubes using a scissors. 12 Grams of sulfamethizol (SM) were admixed with the gelatin cubes, and the resulting admixture was warmed with stirring at 200 rpm for 20 minutes in a water bath heated to a temperature of about 55°–60° C. The warmed admixture was then poured into 300 grams of mineral oil that was previously heated to a temperature of about 55°–60° C. The mineral oil suspension was stirred at 200 rpm for a period of 5 minutes, and then the vessel containing that mineral oil suspension was placed into an ice-water bath and its contents were quickly cooled to a temperature of less than about 5° C. The cooled suspension was stirred at 300 rpm and stirring was continued for 90 minutes while maintaining the suspension temperature at about 5° C. until the gelatin microcapsules so produced had gelatinized substantially completely.

150 Grams of isopropanol at a temperature of 5° C. were added to dehydrate the gelatinized microcapsules and the isopropanol-containing suspension was stirred for an additional 30 minute period at 300 rpm. The dehydrated microcapsules were collected by filtration, washed three times with 60 gram portions of isopropanol cooled to a temperature of about 5°, and then dried using a hand-held hair drier set at its lowest temperature until the odor of isopropanol was no longer detectable.

One gram of the microcapsules so prepared was then immersed in 10 milliliters of 10 volume percent formalin-isopropanol in a covered glass vessel. The suspension so prepared was then refrigerated at a temperature of about 2°–5° C. for a period of 24 hours. The cross-linked gelatin-SM microcapsules so prepared were washed in isopropanol and then dried. The microcapsules so prepared had an average longest dimension of about 1 to about 1000 microns.

If desired, microcapsules prepared as described above may be coated with a bioadhesive or intimately mixed with a bioadhesive to provide a composition of this invention as discussed in Example 4.

EXAMPLE 6

Bioadhesive Laminate Composition

A dispersion was prepared that contained 750 milligrams of sulfanilamide as treating agent, and 600 milligrams of ethyl cellulose as a medicinally inert polymer matrix in 8 milliliters of a solvent containing a 7:2 by volume mixture of toluene and ethanol. 150 Milligrams of castor oil as a plasticizer were added, and the resulting dispersion was homogenized and cast onto an aluminum dish to provide a film having an area of 23.75 cm$^2$ and a thickness of 564-23 microns after drying.

400 Micrograms of poly(2-hydroxyethyl methacrylate) (p-HEMA, Example 2) were dissolved in 3 milliliters of dimethylformamide (DMF). The resulting solution was poured into a glass petri dish and dried to provide a film. The dry film so prepared has an area of 23.75 cm$^2$ and a thickness of 168±8 microns. A second, substantially identical film was also prepared.

Two preparations of swollen polycarbophil were made using bioadhesive particles of 30/40 mesh Tyler size. For each preparation, 160 milligrams of bioadhesive were swollen in a solution containing 0.5 milliliters of DMF and 1.5 milliliters of distilled water.

One side each of the above two p-HEMA films was wetted by a fine spray of DMF. One minute thereafter, the above swollen bioadhesive particles were evenly spread over the surface of each of the wet films using a spatula. The bioadhesive-coated p-HEMA films were then dried at room temperature.

The non-bioahesive-coated surfaces of the p-HEMA films were wet thoroughly by spraying with DMF. Both surfaces of the sulfanilamide-containing ethyl cellulose films were also wet by spraying with DMF.

One wet surface of the sulfanilamide-containing ethyl cellulose film was then contacted with the wet surface of each of the p-HEMA-bioadhesive film to form a laminate composition of this invention. After drying at room temperature, the laminate composition so prepared was cut into rectangular pieces about 2×3 millimeters on a side. The laminate pieces so prepared were loaded into gelatin capsules for oral administration.

The three-layered laminate prepared above contained a bioadhesive to treating agent weight ratio of about 1:2.3.

If desired, the second p-HEMA-bioadhesive film may be eliminated from the above composition to provide another alternative two-layered laminate composition of this invention, or one of the coatings of bioadhesive may be eliminated to provide an alternative three-layered laminate composition of this invention. In addition, the swollen bioadhesive may be applied directly to one or both sides of the wet, sulfanilamide-containing ethyl cellulose film to provide still another composition of this invention in film form. These alternative compositions having bioadhesive disposed on only one surface portion contain a bioadhesive to treating agent weight ratio of about 1:4.7.

EXAMPLE 7

Bioadhesive Film Composition 3.36 Grams of p-HEMA (Example 2) as medicinally inert matrix were dissolved in 13 milliliters of dimethyl formamide (DMF), and 1.44 grams of sulfamethiazole as treating agent were admixed with the resulting solution. The treating agent-matrix solution was poured into a glass petri dish having an area of 63.585 cm$^2$ and dried to form a film. The film so prepared had a thickness of 1000±100 microns.

430 Milligrams of polycarbophil sieved to a 30/40 mesh size were swollen in 6 milliliters of a solution that contained 3 parts of water and 1 part of DMF, by volume. The above-prepared film was wetted by a fine spray of DMF. About one minute thereafter, the swollen bioahesive was evenly spread over the wet surface of the film using a spatula. The film composition of this invention so prepared was then dried at room temperature.

After drying, a second, similar amount of bioadhesive was spread over the second surface of the film composition to form another composition of this invention. The second composition was dried again at room temperature and then cut into rectangularly shaped pieces having dimensions of about 2×3 millimeters. Those pieces were thereafter loaded into a gelatin capsule for use in oral administration.

The weight ratio of bioadhesive to treating agent in the first-described laminate of this Example was about 1:3.3, while the similar weight ratio for the second-described laminate was about 1:1.7.

EXAMPLE 8

Gelatin Microcapsule-Containing Laminate Compositions

The sulfamethiazole-containing microcapsules of Example 5 were utilized to prepare a laminate composition of this invention. 100 Milligrams of those microcapsules were dispersed in a solution containing 250 milligrams of p-HEMA (Example 2) in 4 milliliters of DMF.

That dispersion was poured into a glass petri desh having an area of 23.5 cm$^2$ and then dried to provide a film having a thickness of 400–500 microns. Two- and three-layered laminates of this invention having bioadhesive disposed on one and two surface portions, respectively, were prepared following the procedure of Example 6. Additional laminate compositions of this invention that contain a microencapsulated treating agent such as that of this Example can be prepared as is also discussed in Example 6.

EXAMPLE 9

Rat Serum Treating Agent Levels

Microcapsules having BSA as an encapsulating medicinally inert matrix and chlorothiazide as treating agent were prepared by using ten times the amounts of reagents described in Example 4. The total amount of oil phase was the same as that used in Example 4, but 105 milliliters of petroleum ether and 95 milliliters of $CCl_4$ were used here.

More specifically, one gram of chlorothiazide (DIURIL®, Merck, Sharp & Dohme, Rahway, N.J.) was dispersed in 8.4 milliliters (ml) of a 2.4 weight percent solution of bovine albumin (Fraction V powder, Sigma, St. Louis, Mo.) in 1 millimolar phosphate buffer (pH 7.5) maintained in an ice bath. Crosslinking of the albumin was initiated by the addition of 1.6 ml of 25 percent by volume aqueous solution of glutaraldehyde (Grade II, Sigma, St. Louis, Mo.), resulting in a final glutaraldehyde concentration of 4 percent by volume. The dispersion was then quickly vortexed, drawn into a 20 cc syringe, and immediately injected into a stirring (120–150 rpm) oil phase consisting of 105 ml petroleum ether, 95 ml carbon tetrachloride, and 1 g Span 80 (sorbitan monoleate). Stirring was continued for about one hour; the beads formed were then collected and washed with about 50 ml petroleum ether over suction, dried in an oven at 70° C. for about two hours, and sieved to a 30/40 mesh cut.

Albumin beads free from chlorothiazide (blank beads) were prepared by the same method except that no drug was used.

The albumin beads were characterized with respect to drug content and density. The percent chlorothiazide in the beads was determined as follows. A weighed amount of albumin beads was placed in a measured volume of dimethylformamide, and was shaken for 24 hours on a mechanical shaker. An aliquot of the supernatant was then diluted appropriately and its absorbance was determined on a spectrophotometer (559A UV/VIS, Perkin-Elmer, Norwalk, Conn.) at 330 nanometers (nm) against a dimethylformamide blank. The concentration of chlorothiazide was interpolated from a standard curve, and was converted to percent (wt/wt) chlorothiazide in the ablumin beads.

The approximate density of the beads was determined by the displacement method using a Weld pycnometer.

The albumin beads and polycarbophil (lot #AHR 3260, CH #13430, A.H. Robins Co.) were separately sievered to provide 30/40 mesh Tyler particles. The particles so sized were then loaded into gelatin capsules in a ratio by weight of albumin beads polycarbophil of 3:7 to provide an intimate mixture.

Male Sprague-Dawley rats weighing between 150 and 200 grams were fasted, with free access to water, for 36 to 48 hours prior to in vivo determinations. The animals were anesthetized, and gelatin capsules and 4 milliliters of normal saline were implanted and injected, respectively, into their stomachs as described in Example 3.

Number 4 gelatin capsules were used for these determinations. The capsules contained either 30 milligrams of albumin-chlorothiazine beads plus 70 milligrams of polycarbophil (study) as a composition of this invention, 30 milligrams of albumin-chlorothiazine beads plus 70 milligrams of blank beads (control I), or 9.5 milligrams of chlorothiazine powder (Control II).

The implant bearing rats were caged for recovery. Thereafter, the rats were removed from their cages at various times and placed in the ether chamber for about five minutes. Three to four milliliters of blood were collected by cardiac puncture using a 22 G needle and a 5 milliliter syringe previously wet with heparin.

The collected blood was transferred to a 4 milliliter heparinized blood collection tube (VACUTAINER available from Becton-Dickinson, Rutherford, N.J.) and immediately centrifuged (DYNAC centrifuge, Clay Adams, Parsippany, N.J.) for 15 minutes at about 2000 rpm. The plasma so obtained was removed and stored at −20° C. until anlayzed for its chlorothiazide content.

The concentration of chlorothiazide in the plasma was determined by the high pressure liquid chromatographic (HLPC) method of Burbhaiya et al., *J. Pharm. Sci.*, 70, 291 (1981).

In accordance with that method, 50 microliters of a 40 microgram/milliliter solution of hydroflumethiazide (Bristol Laboratories, East Syracuse, N.Y.) as internal standard were added to 1.0 milliliter of plasma along with 40 milliliters of toluene. After shaking for 10 minutes and 3 minutes of centrifugation, the toluene layer was aspirated and discarded.

To the remaining plasma solution were added 0.5 milliliters of 0.01 molar acetate buffer (pH 3.8) and 5.0 milliliters of ethyl acetate. After shaking for 10 minutes and centrifugation for 3 minutes, 4.0 milliliters of the ethyl acetate layer were transferred to a clean tube, and evaporated to dryness under a gentle stream of nitrogen. The dried material so obtained was reconstituted with 75 microliters of methanol, and 20 microliters of the resulting methanol solution were injected into the HPLC column.

The HPLC system consisted of a solvent pump (Model 110A, Altex Scientific, Berkeley Calif.), a 20 microliter, fixed volume injection valve (Model 210, Altex Scientific), a 10 micron particle size reversed-phase octadecyl column (Lichrosorb RP-18, Alltech Associates, Inc., Deerfield, Ill.), and a single wavelength detector (Model 153, Altex Scientific) set at 280 nanometers. Chromatograms were recorded at a chart speed of 0.5 centimeters/minute. The mobil phase was 30% methanol in 0.01 molar acetic acid, pumped at a flow rate of 1.5 milliliters per minute. Concentrations were determined by the method of peak height ratios.

The results of this study are shown in the graph of FIG. 9. The value at each time point represents the mean of five determinations.

As can be seen from examination of FIG. 9, the blood level of chlorothiazide provided by the composition of this invention (study) was higher than that provided by either of the control compositions over the first six hours after administration, with the peak time for drug in plasma being at about eight hours for the composition of this invention and for control I, but nearer to six hours for the powdered drug (Control II). It is also readily seen that the composition of this invention provided a bioavailability of about two times (1.95±0.14) the amount of treating agent to the blood from about eight hours after administration through the remainder of time during which data were taken.

A study of the passage of gastrointestinal transit of albumin bead and of bioadhesive, polycarbophil-albumin bead dosage forms was also conducted using the beads described in this Example and the surgical procedures described in Example 3. The number of beads found in the stomach and small intestines of the treated rats were counted at a time six hours after surgical administration of the beads.

The results of this study showed that almost 90 percent of the bioadhesive-albumin beads of this invention remained in the stomach after six hours, with very few beads being found beyond the stomach. In the absence of the bioadhesive, the majority of the albumin beads moved at least half-way down the small intestine, with some moving further. Practically no bioadhesive-free albumin beads were found in the stomach after six hours.

The above results clearly illustrate the efficacy of a composition of this invention in an in vivo system. While the release of chlorothiazide from the albumin beads in vivo was relatively rapid, the duration of action and the bioavailability of the chlorothiazide was significantly improved over that obtained with a typical sustained release dosage form. The basis for that improvement demonstrated in this study is the reduced rate of a gastric emptying and subsequent increase in contact time of the bioadhesive-albumin dosage form as compared to a typical sustained release, albumin bead, dosage form. That delay in stomach emptying is caused by the binding of the bioadhesive to the beads and to the gastric mucin/epithelial cell surface.

EXAMPLE 10

Controlled Release Opthalmic Treatments

An aqueous mixture of $^{14}$C-labeled fluorometholone as treating agent and polycarbophil as bioadhesive was prepared. The $^{14}$C-labeled fluorometholone was thereby sorbed into the bioadhesive particles. The particles so prepared were filtered, dried, crushed and screened to provide a $^{14}$C-labeled fluorometholone-containing particulate composition of this invention.

The composition so prepared was resuspended in water (study), and another aqueous composition containing $^{14}$C-labeled fluorometholone, but no bioadhesive (control) was also prepared. The thus prepared compositions were separately instilled into the precorneal pockets of separate rabbits. The radioactivity present in the corneas and aqueous humors of the treated rabbits was measured at various times after administration and resulting contact of the study and control compositions with the mucosa of the eye.

The results of this determination showed that the composition of this invention provided a higher concentration of the treating agent in both tissues as well as a prolongation of the presence of the treating agent in both tissues. These results provide yet another example of the in vivo effficacy of a composition of this invention.

EXAMPLE 11

Controlled Release Opthalmic Composition

Another controlled release composition of this invention was prepared in which the treating agent, fluorometholone, was entrapped within the bioadhesive during the polymerization of the bioadhesive. Here, 0.133 grams of fluorometholone was premixed with 20 grams of acrylic acid, 0.03 grams of 2,5-dimethyl-1,5-hexadiene and 0.2 grams of benzoyl peroxide.

The mixture so prepared was then added with stirring to a refluxing aqueous composition containing 160 grams of MgSO$_4$-7H$_2$O, and polymerization, recovery, drying of the resulting treating agent-containing bioadhesive particles was carried out following the general procedures discussed in Example 1. The dried composition of this invention so prepared was then crushed and sieved to provide particles that pass throught a 100 mesh sieve screen (Tyler).

The particles so prepared were then added to a saturated aqueous solution of fluorometholone as a further composition of this invention suitable for contacting opthalmic mucosa. The use of a saturated solution of the treating agent in conjunction with a composition of this invention containing the same treating agent tends to retard premature release of the treating agent from the composition into the physiologically tolerable carrier in which the composition is suspended.

EXAMPLE 12

Bioadhesion as a Function of pH Value

Figure 10:
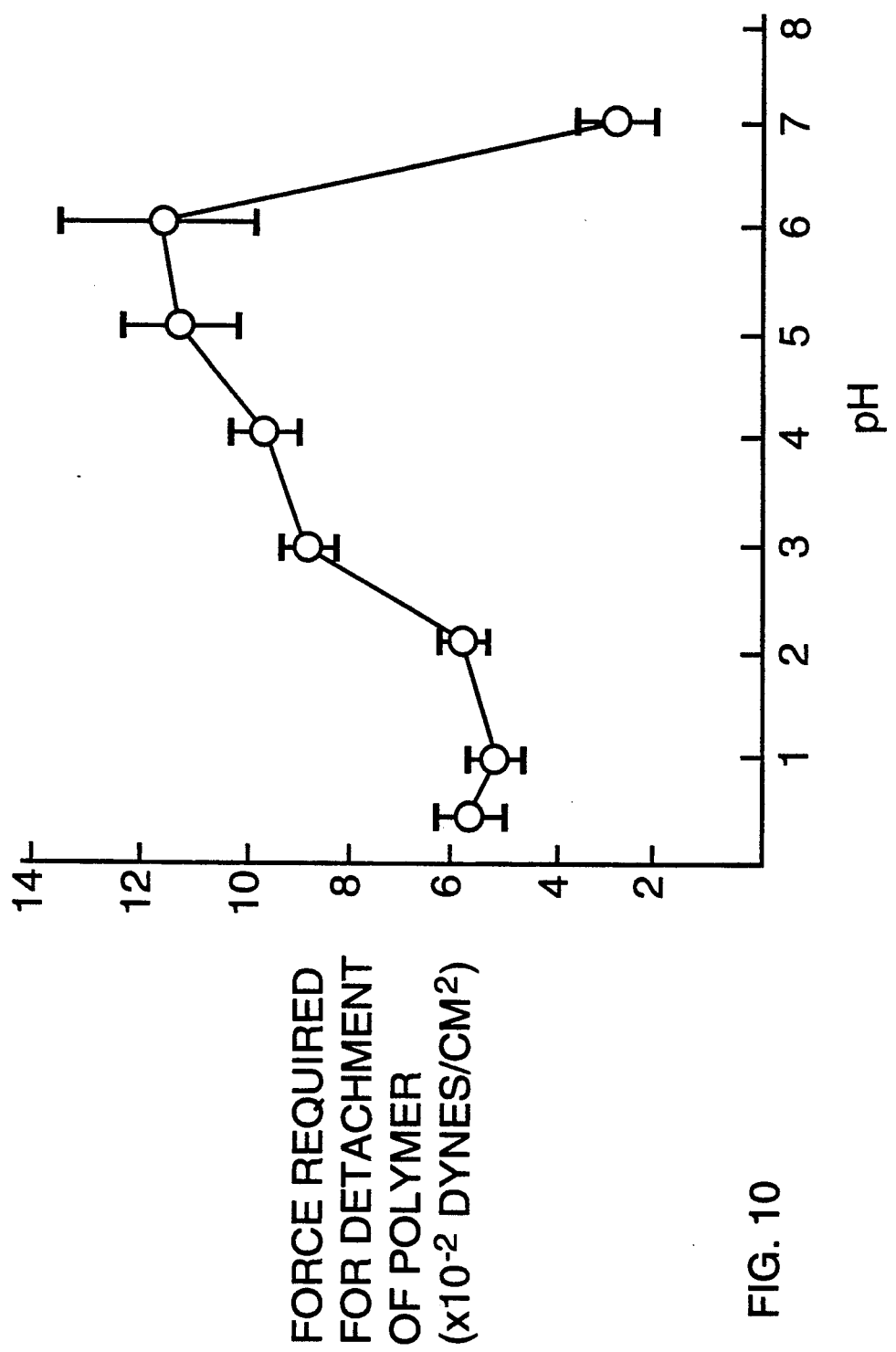
FIG. 10 is a graph illustrating the force (dynes $\times 10^{-2}$/cm$^2$) for detatching a bioadhesive polymer reaction product of acrylic acid copolymerized with 0.3 weight percent 3,4-dihydroxy-1,5-hexadine having a density of 1.56 grams/cubic centimeter (g/cc) versus pH value.

The force measured to separate a bioadhesive polymer that is the reaction product of the polymerization of acrylic acid with 0.3 weight percent of 3,4-dihydroxy-1,5-hexadiene that had a density of 1.56 g/cc is shown in FIG. 10. As is seen from the Figure, the maximum adhesion was observed at a pH value of about 5 to about 6. That maximum value was more than twice the adhesive force required for the separation at pH values of 0.46, 1.42 or 2.0. As is also seen, adhesion provided by that bioadhesive polymer was substantially reduced at pH value of 7. That reduction was statistically significant in a Student's t-test, p less than 0.01. Bioadhesive forces were measured as discussed previously in Example 2.

The foregoing is intended as illustrative of the present invention but not limiting. Numerous variations and modifications may be effected without departing from the true spirit and scope of the novel concepts of the invention.

What is claimed is:

1. A controlled release ophthalmic treatment composition comprising a bioadhesive and an effective amount of an ophthalmic treating agent, said bioadhesive comprising a water-swellable, but water-insoluble, particulate cross-linked carboxyl-functional polymer said polymer derived from monomers selected from the group consisting of acrylic acid, methacrylic acid, fumaric acid, maleic acid, maleic anhydride, itaconic acid, crotonic acid and mixtures thereof having particles sized so that visual impairment is substantially minimized when said composition is contacted with a mucous membrane of the eye, said polymer containing (a) a plurality of repeating units of which at least about 80 percent contain at least one carboxyl functionality, and (b) a cross-linked agent substantially free from polyalkenyl polyether said agent selected from the group consisting of divinyl benzend, N,N-dialkylacrylamide, 3,4-dihydroxy-1,5-hexadiene and 2,5-dimethyl-1,5-hexadiene, said agent being from about 0.05 to 2.0 weight.

2. A controlled release ophthalmic treatment composition as recited in claim 1 wherein said bioadhesive and said treating agent are intimately admixed substantially uniform.

3. A controlled release ophthalmic treatment composition as recited in claim 1 wherein at least about 90 percent of said polymer repeating units contain at least one carboxyl functionality.

4. A controlled release ophthalmic treatment composition as recited in claim 1 wherein at least about 95 percent of said polymer repeating units contain at least one carboxyl funtionality.

5. A controlled release ophthalmic treatment composition as recited in claim 1 wherein said polymer contains about 0.01 to about 2 percent by weight of polymerized cross-linking agent.

6. A controlled release ophthalmic treatment composition as recited in claim 1 wherein said carboxyl functionality is provided by polymerized acrylic acid.

7. A controlled release ophthalmic treatment composition as recited in claim 1 wherein at least about 95 percent of said polymer repeating units contain at least one carboxyl functionality provided by acrylic acid, and said polymer contains about 0.01 to about 2 percent by weight of polymerized cross-linking agent.

8. A controlled release ophthalmic treatment composition as recited in claim 7 wherein said cross-linking agent is 3,4-dihydroxy-1,5-hexadiene.

9. A controlled release ophthalmic treatment composition as recited in claim 7 wherein said cross-linking agent is divinyl benzene.

10. A controlled release ophthalmic treatment composition as recited in claim 7 wherein said cross-linking agent is 1,5-dimethyl-1,5-hexadiene.

11. A controlled release ophthalmic treatment composition as recited in any one of claims 1-10, inclusive, wherein said ophthalmic treating agent constitutes an anti-inflammatory agent.

12. A controlled release ophthalmic treatment composition as recited in claim 11 wherein said anti-inflammatory agent is fluorometholone.

13. A method of controlled release ophthalmic treatment comprising the steps of:
(A) providing a controlled release ophthalmic treatment composition comprising a bioadhesive and an effective amount of ophthalmic treating agent, said bioadhesive comprising a water-swellable, but water-insoluble, particulate cross-linked carboxyl-functional polymer derived from monomers selected from the group consisting of acrylic acid, methacrylic acid, fumaric acid, maleic acid, maleic anhydride, itaconic acid, crotonic acid, and mixtures thereof having particles sized so that visual impairment is minimized when said composition is contacted with a mucous membrane of the eye, said polymer containing (a) a plurality of repeating units of which at least about 80 percent contain at least one carboxyl functionality, and (b) a cross-linking agent substantially free from polyalkenyl polyether said agent selected from the group consisting of divinyl benzene, N,N-dialkylacrylamide, 3,4-dihydroxy-1,5-hexadiene and 2,5-dimethyl-1,5-hexadiene, said agent being from about 0.05 to 2.0 weight percent.

14. A method as recited in claim 13 wherein said bioadhesive and said treating agent are intimately admixed substantially uniformly.

15. A method as recited in claim 13 wherein at least about 90 percent of said polymer repeating units contain at least one carboxyl functionality.

16. A method as recited in claim 13 wherein said polymer contains about 0.01 to about 2 percent by weight of polymerized cross-linking agent.

17. A method as recited in claim 13 wherein said carboxyl functionality is provided by polymerized acrylic acid.

18. A method as recited in claim 13 wherein said anti-inflammatory agent is fluorometholone.

19. A method as recited in claim 18 wherein said anti-inflammatory agent is fluorometholone.

* * * * *